(12) United States Patent
Dycher et al.

(10) Patent No.: US 11,911,539 B2
(45) Date of Patent: Feb. 27, 2024

(54) DEVICE FOR DISPENSING, IN PARTICULAR FOR VAPORIZING, VOLATILE SUBSTANCES, IN PARTICULAR FRAGRANCES AND/OR ACTIVE AGENTS

(71) Applicant: CTR, LDA, Samora Correia (PT)

(72) Inventors: David Dycher, Isle of Man (GB); Pedro Queiroz Vieira, Belas (PT)

(73) Assignee: CTR, LDA, Samora Correia (PT)

( * ) Notice: Subject to any disclaimer, the term of this patent is extended or adjusted under 35 U.S.C. 154(b) by 0 days.

(21) Appl. No.: 17/539,634

(22) Filed: Dec. 1, 2021

(65) Prior Publication Data
US 2022/0088254 A1   Mar. 24, 2022

Related U.S. Application Data

(63) Continuation of application No. 16/310,259, filed as application No. PCT/EP2016/001008 on Jun. 16, 2016, now abandoned.

(51) Int. Cl.
*A61L 9/03* (2006.01)

(52) U.S. Cl.
CPC ......... *A61L 9/037* (2013.01); *A61L 2209/133* (2013.01)

(58) Field of Classification Search
CPC .......................... A61L 9/037; A61L 2209/133
See application file for complete search history.

(56) References Cited

U.S. PATENT DOCUMENTS

| | | | | |
|---|---|---|---|---|
| 3,067,310 A | * | 12/1962 | Walz | H05B 3/26 219/541 |
| 4,952,903 A | * | 8/1990 | Shibata | H05B 3/265 204/426 |
| 4,968,487 A | | 11/1990 | Yamamoto et al. | |
| 5,394,506 A | | 2/1995 | Stein et al. | |
| 5,903,710 A | * | 5/1999 | Wefler | A01M 1/2077 261/142 |
| 6,563,091 B2 | | 5/2003 | Vieira | |
| 7,629,001 B2 | | 12/2009 | Davis et al. | |
| 9,242,020 B2 | | 1/2016 | Ihle et al. | |
| 2004/0190883 A1 | | 9/2004 | Kompara et al. | |

(Continued)

FOREIGN PATENT DOCUMENTS

| | | |
|---|---|---|
| CN | 87107947 A | 8/1988 |
| CN | 2448110 Y | 9/2001 |

(Continued)

*Primary Examiner* — Thien S Tran
(74) *Attorney, Agent, or Firm* — Laurence A. Greenberg; Werner H. Stemer; Ralph E. Locher

(57) ABSTRACT

A device for dispensing, in particular for vaporizing, volatile substances such as fragrances and/or active agents, includes a container and a capillary element in contact with said substance to be dispensed that conveys said substance to at least one substance dispensing region by a capillary effect. At least one electrical heating element adjoins said at least one capillary element. An electrical connection element supplies said electrical heating element with electrical energy. The heating element is a constituent part of said container and said container can be releasably connected to said electrical connection element. An electrical contact device is provided for electrically connecting said heating element to said electrical connection element in a releasable manner.

35 Claims, 16 Drawing Sheets

(56) References Cited

U.S. PATENT DOCUMENTS

| | | | |
|---|---|---|---|
| 2005/0155985 A1* | 7/2005 | Meyer | A61L 9/037 222/146.2 |
| 2008/0138051 A1 | 6/2008 | Velazquez et al. | |
| 2010/0176213 A1 | 7/2010 | Belongia et al. | |

FOREIGN PATENT DOCUMENTS

| | | |
|---|---|---|
| CN | 101243788 A | 8/2008 |
| CN | 101557833 A | 10/2009 |
| CN | 103283303 A | 9/2013 |
| DE | 3737272 A1 | 6/1988 |
| EP | 0716807 A1 | 6/1996 |
| EP | 0945062 A1 | 9/1999 |
| EP | 1247447 A1 | 10/2002 |
| EP | 1270020 A1 | 1/2003 |
| EP | 1270022 A1 | 1/2003 |
| EP | 1844795 A1 | 10/2007 |
| GB | 2354444 A | 3/2001 |
| GB | 2356814 A | 6/2001 |
| WO | 9811924 A1 | 3/1998 |
| WO | 9846282 A1 | 10/1998 |
| WO | 9858692 A1 | 12/1998 |
| WO | 0121226 A1 | 3/2001 |
| WO | 2004068945 A1 | 8/2004 |
| WO | 2005011373 A2 | 2/2005 |
| WO | 2005021052 A1 | 3/2005 |
| WO | 2008072109 A2 | 6/2008 |
| WO | 2012052321 A1 | 4/2012 |
| WO | 2013012442 A1 | 1/2013 |
| WO | 2013188493 A1 | 12/2013 |
| WO | 2014022164 A2 | 2/2014 |
| WO | 2016180663 A1 | 11/2016 |

\* cited by examiner

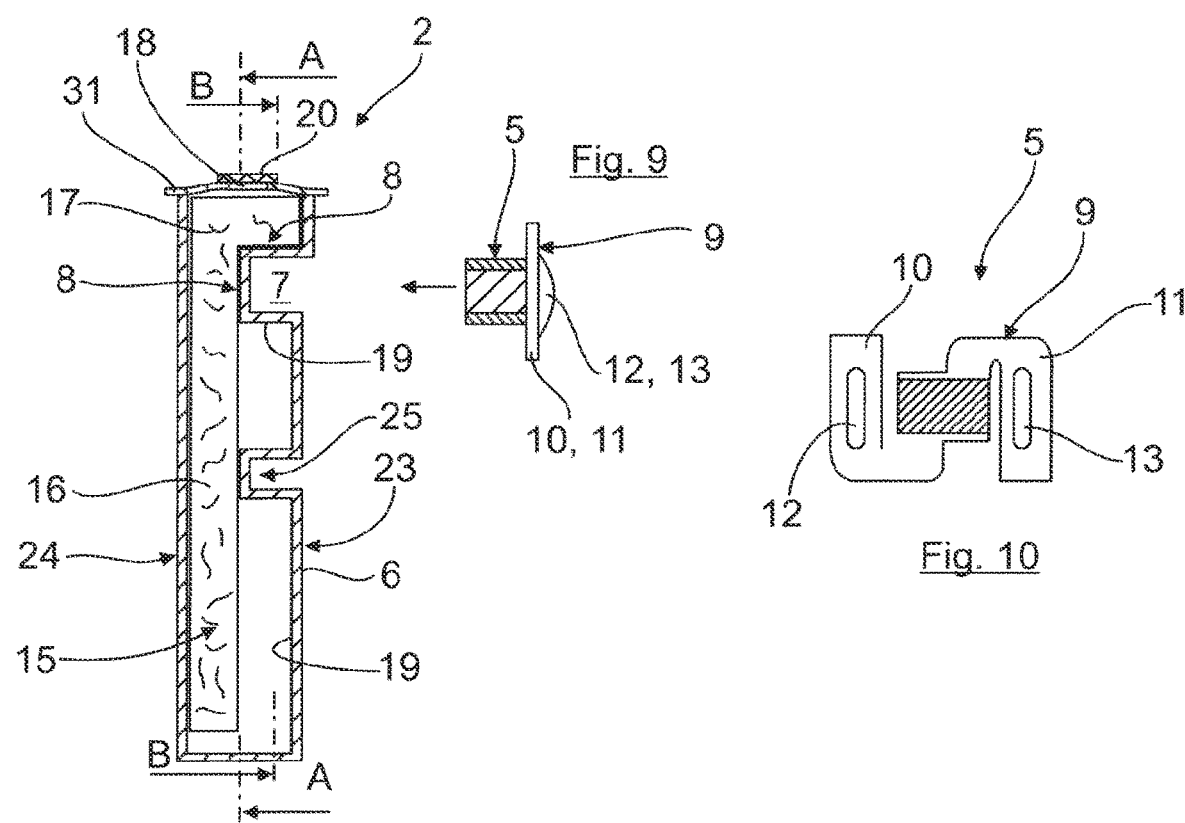

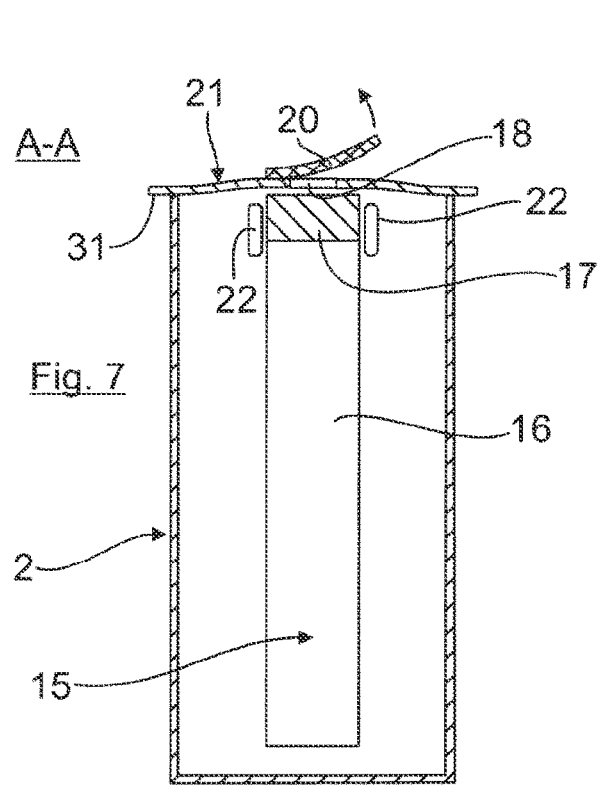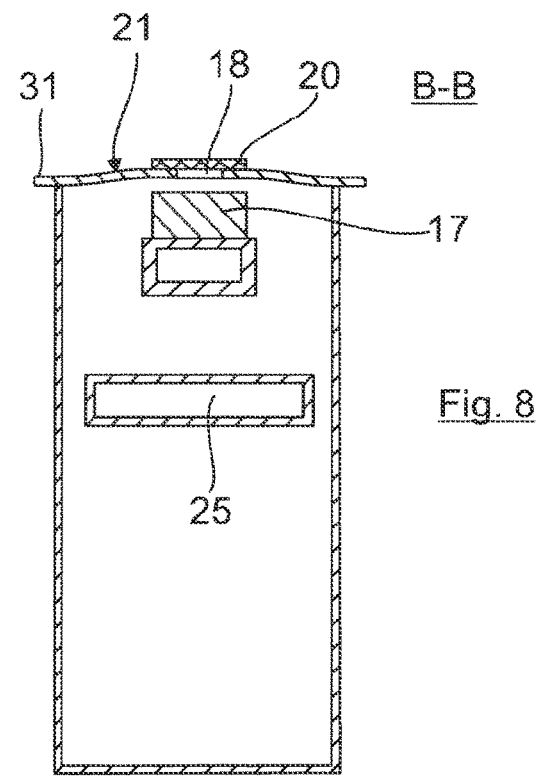

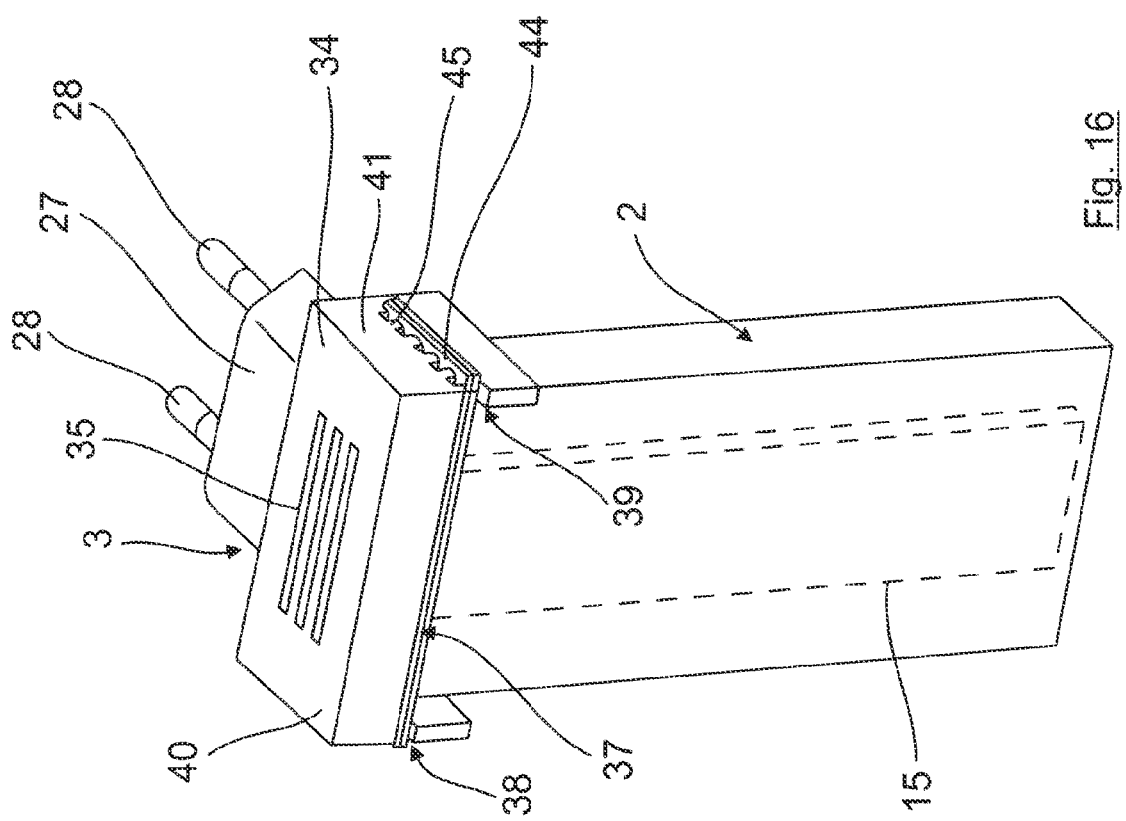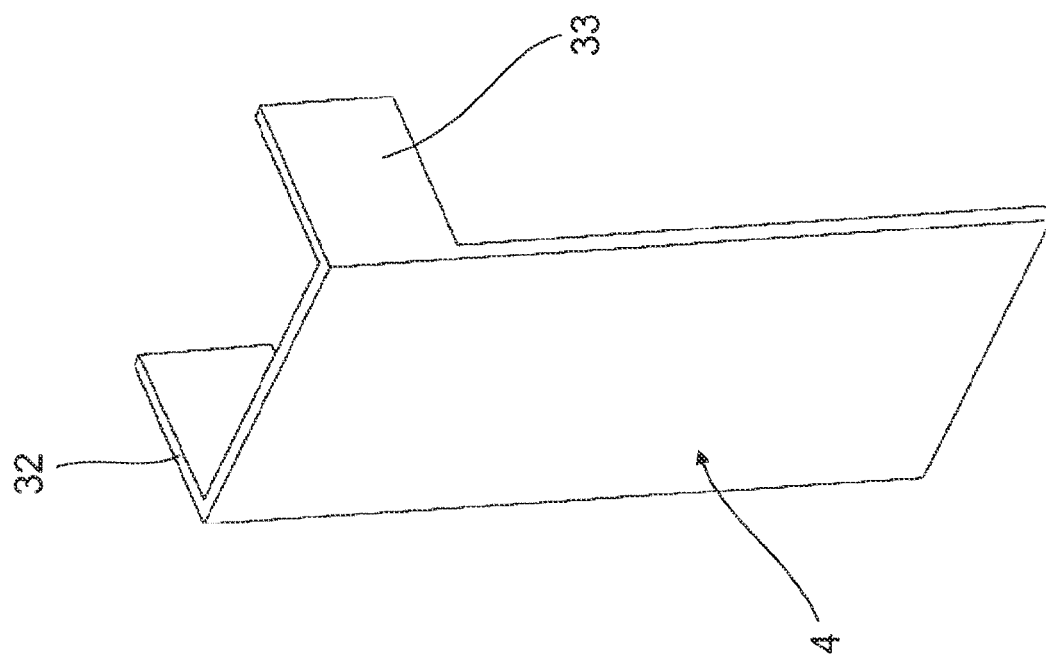
Fig. 16

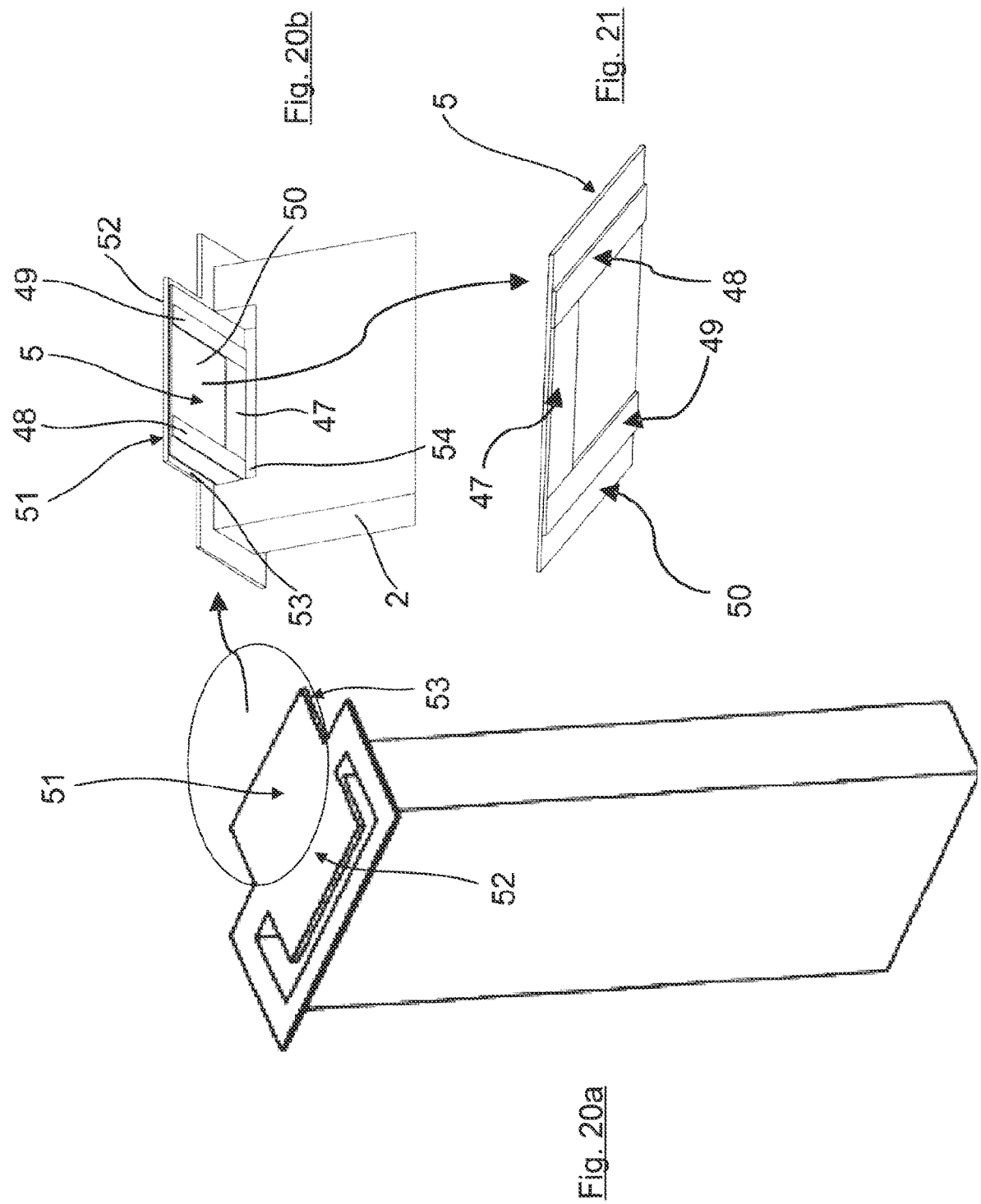

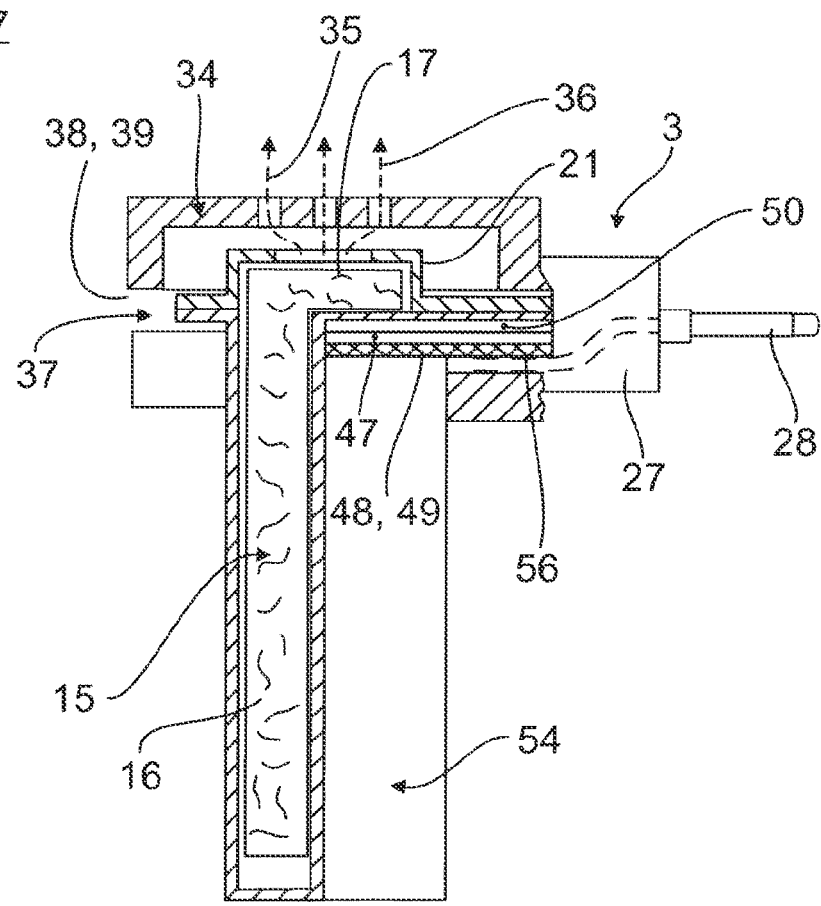

US 11,911,539 B2

DEVICE FOR DISPENSING, IN PARTICULAR FOR VAPORIZING, VOLATILE SUBSTANCES, IN PARTICULAR FRAGRANCES AND/OR ACTIVE AGENTS

CROSS-REFERENCE TO RELATED APPLICATION

This application is a continuation of patent application Ser. No. 16/310,259, filed Dec. 14, 2018; which was a § 371 national stage filing of international application No. PCT/EP2016/001008, filed Jun. 16, 2016, which designated the United States; the prior applications are herewith incorporated by reference in their entirety.

FIELD AND BACKGROUND OF THE INVENTION

The invention relates to a device for dispensing, in particular for vaporizing, volatile substances, in particular fragrances and/or active agents. The device has a container for a substance to be dispensed. At least one capillary element which is arranged at least in part in said container, is in contact with said substance to be dispensed and conveys said substance by means of capillary action to at least one substance dispensing region. At least one electrical heating element adjoins said at least one capillary element. An electrical connection element supplies said at least one electrical heating element with electrical power. In addition, said invention relates to a container for receiving volatile substances that is suitable for use in said dispensing device.

Devices for dispensing, in particular for vaporizing, volatile substances, in particular fragrances and/or active agents, are known generally and as a rule include a container in which a substance to be dispensed is received. A wick, which projects beyond the container by way of a free wick end and is in contact with the substance to be dispensed in such a manner that said substance is conveyed in the direction of the free wick end by means of the capillary action of the wick, is arranged in the container as a capillary element. The free wick end regularly has associated therewith a heating element, in particular an electrical heating element, by means of which the free wick end is able to be acted upon with heat in order to be able to dispense or vaporize the substance accumulating in the free wick end even quicker to the surrounding area. Such a design is disclosed, for example, in WO 98/58692 A1. Insofar as the substance received in the container is vaporized, the container is replaced by a new, fresh container in which either the same substance to be dispensed is contained or, however, another substance to be vaporized can also be contained.

In the case of said known devices, the electrical heating element is arranged in the interior of the housing and is held there, the electrical heating element being formed regularly by a so-called heating block which is produced from a ceramic material and in which an electrical resistance element is received. If the resistance element is traversed by a current, the heating block is heated and then outputs the heat to the free end of the wick which projects into the heating block such that the substance, sucked up by the wick by means of the capillary effect, is vaporized and is able to escape via the housing into the surrounding area.

Electrical conductors, which are run to a connection plug which in turn can be connected to a socket, project out of the heating block for supplying power.

In the case of such a conventional design with a wick which projects into the region of a heating block, relatively high temperatures and consequently relatively large structures are required overall for higher vaporizing rates. Structural freedoms are consequently relatively restricted and the design requires a plurality of individual components overall. This, in turn, means relatively high production and assembly expenditure in conjunction with the final assembly of such devices.

SUMMARY OF THE INVENTION

Accordingly, it is the object of the present invention to create a device for dispensing, in particular for vaporizing, volatile substances, in particular fragrances and/or active agents, by means of which a compact, small design and/or a reduction in the temperatures necessary for effective vaporizing is possible. In addition, it is an object of the present invention to create a container for receiving volatile substances which is suitable, in particular, for use in conjunction with a device according to the invention.

Said object is achieved with the features of the independent patent claims. Advantageous designs are the object of the subclaims.

There is claimed a device for dispensing, in particular for vaporizing, volatile substances, in particular fragrances and/or active agents, having a container in which a substance to be dispensed is receivable or received. Additionally provided is at least one capillary element, for example in the form of a wick, which is arranged at least in part in the container, is in contact with the substance to be dispensed and conveys said substance by means of capillary action to at least one substance dispensing region, preferably in the direction of at least one outlet opening of the container which is assigned to the substance dispensing region. Additionally provided is at least one electrical heating element which adjoins the at least one capillary element and is able to act on said capillary element with heat. Additionally provided is an electrical connection element, by means of which the at least one electrical heating element can be supplied with electrical power. It is provided according to the invention that the at least one electrical heating element is a constituent part of the container, preferably realizing a separate component or a separate structural unit, that the container is releasably connectable to the electrical connection element and that an electrical contact device is provided, by means of which the at least one electrical heating element is releasably and electrically connectable to the connection element.

The achievement with the solution according to the invention is that the at least one electrical heating element is no longer a constituent part of a housing into which the container is inserted but that the at least one heating element is now a constituent part of the container itself, the at least one electrical heating element of the container having then to be connected, for supplying power, to the electrical connection element which also realizes, in a preferred manner, a separate component or a separate structural unit.

As a result of the inclusion or integration of the at least one electrical heating unit in the container, new structural degrees of freedom are produced, for example to the effect that the at least one electrical heating element is thus able to be arranged (in a manner described in more detail below) directly adjoining the capillary element such that said capillary element is able to be heated in a capillary element region to be heated in an effective manner as a result of heat conduction, as a result of which optimized vaporization of the substance to be dispensed is achieved at comparatively lower temperatures overall.

Furthermore, in conjunction with integrating or including the at least one electrical heating element in the container assembly in such a manner, an relatively compact and small design overall is produced which in turn can contribute advantageously to reducing the overall size and dimension of a device for dispensing volatile substances.

Furthermore, this also produces another production and manufacturing technology where the at least one electrical heating element is installed as early as during the manufacturing of the container such that the vertical range of manufacture can be advantageously reduced as a result.

The term "substance to be dispensed" is to be understood here specifically in a broad sense and includes all substances which can be conveyed by means of the capillary action of a wick as a capillary element. Along with volatile substances, these can also be specifically gel-like or other suitable substances.

The electrical contact device has simply to make an electrical connection possible between the at least one electrical heating element, which forms a constituent part of the container, and the electrical end element and further also to make the releasable connection between said two structural units possible. The electrical contact device, by means of which the at least one electrical heating element is electrically and releasably connectable to the electrical connection element, can consequently be realized in the most varied of ways, for example as an electrical contact device which makes wireless power transfer possible (also designated as contactless power transfer, as cable-free power transfer or as contactless power transfer) where the electrical power is transmitted in a non-contact manner to the at least one electrical heating element. In principle, in particular also in the case of non-contact-free power transfer, it is consequently implicit that the electrical contact device can be a constituent part of the at least one electrical heating element at least in part and/or a constituent part of the electrical connection element at least in part. This means, in other words, that the electrical contact device can be a constituent part of the at least one electrical heating element in its entirety or, as an alternative to this, can be a constituent part of the electrical connection element in its entirety or, as a further alternative to this, can be realized such that part of the electrical contact device is a constituent part of the electrical heating element and a further part of the electrical contact device is a constituent part of the electrical connection element.

According to a particularly preferred specific design, the releasable connection between the container and the electrical connection element is produced in part or entirely by the electrical contact device, which can consequently produce in a dual function at the same time the releasable connection and fixture between the at least one electrical heating element and the electrical connection element and further, at least in part, also the releasable connection between the container as a whole and the electrical connection element.

The releasable connection between the container and the electrical connection element and/or between the at least one electrical resistance element and the electrical connection element can be effected, in this case, in different ways, a positive locking connection, in particular a latching connection as a positive locking connection, and/or a non-positive locking connection being preferred.

According to a further particularly preferred specific design, the electrical connection element can comprise a holding device, by means of which the container is held on the electrical connection element. Such a holding device on the electrical connection element enables simple positioning and fixing of the container in a defined position, thus, for example, in the region of the at least one electrical heating element, as a result of which simple electrical contacting between the at least one electrical heating element and the electrical connection element is possible by means of the electrical contact device, which is, once again, advantageous for a compact, small design of the device overall.

According to a further particularly preferred specific design, the electrical contact device can comprise contact elements which are arranged on the at least one electrical heating element and are spaced apart from one another, connection contacts, by means of which the contact elements are connected so as to be electrically conductive in the mounted state, being assigned to said contact elements on the electrical connection element, preferably in the region of a holding device. Such a design produces a particularly functionally reliable electrical connection between the electrical contact device of the at least one electrical heating element and the electrical connection element which ultimately achieves the supply of power.

The container and/or the electrical connection element, preferably a holding device of the electrical connection element, can also comprise at least one stop element by means of which the container is positionable in the mounted state such that the at least one electrical heating element is connectable or connected electrically to the electrical connection element by means of the electrical contact device. Particularly preferred, in this connection, is an embodiment where the container is positioned in the mounted state on account of the at least one stop element such that contact elements of the electrical contact device, which are arranged on the at least one electrical heating element, are assigned to connection contacts of the electrical connection element and are connectable or connected to the same so as to be electrically conductive.

The electrical connection element preferably comprises a plug (specifically also includes a design with a cable and a plug arranged thereon), by means of which, for example, a connection to an electrical socket is possible. Particularly preferred in this context is an embodiment where the electrical connection element is formed by a plug which comprises the holding device. It can then be provided in a particularly preferred manner, in this connection, that the holding device is fixedly connected to the plug, for example is integrally molded on the plug. It can also be provided further, as an alternative to this or in addition to it, that the electrical connection element is a one-piece component which is produced, for example, by injection molding. With such a design, the large variety of components is reduced and an electrical connection element which overall is cost-efficient and simple to produce is created. In addition, however, the plug is also able to be held on the electrical connection element so as to be rotatable.

In principle, there are different possibilities for including or integrating the at least one electrical heating element in the container. Generally speaking, this can be effected, for example, such that the at least one electrical heating element forming the constituent part of the container is arranged in such a manner on the container, preferably on an outside surface of the container, and/or on a constituent part of the container, that the at least one electrical heating element transfers heat to the container and/or to a capillary element region to be heated, which is assigned to the at least one electrical heating element, by means of heat conduction. Heat conduction is to be understood here as heat transfer where the heat is transferred from a region of higher temperature to a region of lower temperature through bodies which adjoin each other and touch each other in a contact region (heat transfer region). Such warming or heating by means of heat conduction enables particularly effective and optimized heating of the capillary element region to be heated and consequently optimized dispensing or vaporizing of the substance.

Particularly preferred is an embodiment where the at least one electrical heating element abuts, and/or is fixed, in particular flatly, against the outside surface of a container wall of the container in a heat transfer region, in a preferred manner abuts and/or is fixed, in particular flatly, in a—for particularly preferred heat transfer by means of heat conduction—substantially gap-free or direct bearing connection against the outside surface of the container. As a result, the at least one electrical heating element can transmit heat to the container wall directly or through direct contact by means of heat conduction. In said context, it is particularly advantageous according to a particularly preferred embodiment that the container wall is produced, at least in the heat transfer region, from a heat-conducting or a good heat-conducting material. Such an outside arrangement of the at least one electrical heating element can be realized in a particularly simple and functionally reliable manner.

Particularly preferred in said context is additionally a design where the at least one capillary element abuts and/or is fixed, in particular flatly, against the inside surface of the container wall of the container by way of a capillary element region to be heated at least in the heat transfer region, in a preferred manner abuts or is fixed directly or in a bearing connection or gap-free against the inside surface, in particular flatly, in such a way that the container wall transfers the heat to the capillary element region to be heated by means of heat conduction. As a result, according to a particularly preferred specific design, heat can consequently be transferred by means of heat conduction from the at least one electrical heating element via the container wall, which is produced from a heat-conducting material, in the heat transfer region immediately and directly to the capillary element or the capillary element region to be heated. This results in the previously named lower heating element temperatures in conjunction with a degree of efficiency of the vaporizing device which is still very good, in particular also in conjunction with an excellent capability to control the substance dispensing.

According to a preferred realization variant, the container can comprise a container-side holder for the at least one electrical heating element on the outside wall or on the outside surface of the container wall, said container-side holder already being realized or integrally molded on the outside wall, for example during the production of the container, by way of which holder the at least one electrical heating element is held on the container.

The container-side holder can be formed, in this case, for example, by a receiving element or indentation, which is realized in the outside wall or on the outside surface of the container wall of the container, for example is molded into the outside wall during the production of the container, and in which receiving element or indentation the electrical heating element is then correspondingly received, and for optimized heat transfer is preferably received abutting against the wall of the container or in a manner adapted to its shape and contour.

According to a particularly advantageous embodiment, an electrical contact device forming a constituent part of the electrical heating element can comprise, in principle, at least one, preferably plate-shaped, contact region that is flat and/or extends substantially parallel to the outside wall of the container and/or is arranged or rests on the outside wall of the container and comprises the contact elements, in particular in the form of contact pins or contact elevations. Particularly preferred, in this connection, is a specific embodiment where the electrical heating element is inserted in such a manner in the receiving element or indentation that the electrical contact device realizes a flat and/or plate-shaped contact region which rests on the outside wall of the container and has raised contact elements. Such a design is small and compact overall and additionally enables a simple and functionally reliable possibility for connection to the electrical connection element.

Furthermore, the electrical contact device can be provided on its contact region, which comprises raised contact elements, with a cover, preferably with a cover which is releasably fixable on and/or adherable to the contact surface, through which cover the contact elements project for connection to the connection contact of the electrical connection element. Such a cover enables the attachment of a label or a marking and/or contributes to increasing the functional reliability of the device overall.

The at least one electrical heating element can be formed by a, preferably pill-shaped and/or disk-shaped and/or flat, electrical resistance element which comprises the electrical contact device or is coupled with or connected to the electrical contact device. It is provided, in this connection, in a preferred manner that the electrical contact device is formed by at least one flat contact plate which comprises one or multiple contact elements. The electrical resistance element is preferably a PTC resistance element, that is to say a resistor with a positive temperature coefficient (PTC), which has the advantage of being substantially self-regulating and not needing an electrical control unit in order to limit the maximum heating current such that there is no risk of overheating.

The holding device of the electrical connection element is preferably realized such that it encompasses the container, at least in regions, on the container outside wall, preferably in the region of the at least one electrical heating element. So as to save material, in this case, the holding device can be simply a U-shaped bracket or, however, also a relatively stable holding ring, both of which in a preferred manner are relatively small compared to the container and only extend over a part region of the container or only cover and/or overlap a part region of the container. In principle, the holding device could, however, also be a pocket-shaped receiving element or the like, in which the container is then correspondingly inserted.

Particularly preferred is additionally a specific design where recesses are assigned to the contact elements, which are preferably formed by contact pins or contact elevations, on the electrical connection element, preferably in the region of a holding device of the electrical connection element, in which recesses the contact elements, in particular also for the fixing or shared-fixing of the container on the electrical connection element, engage in the mounted state in a positive locking manner, in particular in a latching locking manner, and are each connected there to a connection contact of the electrical connection element so as to be electrically conductive.

Further preferred is a specific embodiment where the holding device is formed by a holding ring which, in the mounted state, encompasses the container which is insertable into the holding ring (and removable out of the holding ring), preferably encompasses it such that the holding ring abuts at least in regions against the container outside wall.

It is provided in a further preferred manner in this conjunction that the holding ring is elastically flexible at least in regions for realizing an elastically flexible wall region when inserting (and removing) the container, the electrical contact device of which comprises raised contact elements. This ensures that the holding ring, when the container is inserted into the holding ring causing the contact pins or contact elevations to abut against the inside wall region of the holding ring surrounding the recesses, extends elastically at least in regions until the contact pins or contact elevations are in an engagement position at the level of the recesses, in which engagement position the extended wall region of the holding ring springs back to produce the positive locking connection. Analogously, when the container is removed, the contact pins or contact elevations move out of engagement with the recesses and, as a result, once again the contact pins and contact elevations move into abutment against the inside wall region of the holding ring surrounding the recesses, as a result of which said holding ring extends elastically and the container is able to be moved out of engagement with the holding ring.

The electrical heating element, according to a particularly preferred design of said same and in conjunction with all embodiments of said inventive concept described here, in particular however with a device as claimed, can be an electrical resistance element and comprise as heating layer a resistance layer which is preferably assigned to a capillary element region to be heated and/or is film-like. Such a resistance layer as heat layer, as will be shown in more detail below, enables a particular advantageous realization of an electrical heating device by a flexible and/or printed resistor. In said context, it is provided in a further preferred manner that said electrical contact device comprises feed lines which are connected or connectable to said resistance layer, by way of which said electrical connection between said resistance layer and said electrical connection element is producible.

According to a specific design, it is possible to provide, for example, two feed lines which are spaced apart from one another and comprise an electrical connection to the resistance layer which is located in the space between.

In a preferred manner, the resistance layer itself forms a PTC resistance element, that is to say a resistance element with a positive temperature coefficient (PTC). A particular advantage of said PTC resistance layer as resistance element is that, as a result, self-regulating heating is created which manages without an electronic control unit in order to delimit the maximum heating current.

Such resistance layers can be additionally adapted in the simplest manner as regards size and/or dimensions precisely to the capillary element region to be heated, in particular can correspond to the same as regards size and/or dimension such that it is possible to heat the capillary element region to be heated in a particularly effective manner.

In principle, in connection with the resistance layer, there are diverse possibilities to arrange the same. Thus, the resistance layer, preferably the resistance layer together with the feed lines, is arranged or applied, on the one hand, directly or, as an alternative to this, indirectly with the interposition of at least one intermediate layer, preferably at least one intermediate layer produced from an electrically insulating and/or heat-conducting material, in a heat transfer region on the outside surface of the container wall, which is produced at least in said region from a heat conducting material. In order to ensure in the desired manner that the electrical heating element transfers heat by means of heat conduction to the container wall and from there onto the capillary element region to be heated, it is further provided that in the heat transfer region, the capillary element region to be heated abuts against the inside surface of the container wall, preferably flatly, in a bearing connection.

The electrical heating element comprises in a preferred manner a carrier layer as substrate, on which the resistance layer is applied, preferably as a film layer and/or together with the feed lines, wherein it is provided in a preferred manner that the carrier layer and the resistance layer, as well as, where applicable, together with the feed lines, are realized in a flexible manner for realizing an electrical heating element which is flexible overall. The carrier layer as substrate allows the resistance layer or the resistance layer together with the feed lines to be applied in a particularly advantageous manner, for example to be imprinted, for example in conjunction with a silk-screen printing process. A flexible electrical heating element additionally makes possible, on the one hand, a simple bearing connection against the most varied geometries. In addition, the flexible electrical heating element realized in this manner can then be stored, for example, as piece or rolled goods, from which the required electrical resistance element can simply be cut to length.

According to a particularly preferred embodiment, the carrier layer realizes the at least one intermediate layer.

The electrical heating element can further comprise a, preferably flexible, protective layer which screens or covers, at least in regions, the resistance layer which was applied on the carrier layer, preferably the resistance layer which was applied on the carrier layer together with the feed lines.

Particularly preferred, in this connection, is a design where the not necessarily, but preferably flexible, resistance layer is formed by an electrically conductive ink or paint which comprises a resistance function, in a preferred manner an ink or paint comprising a PTC function. In a particularly advantageous manner, such a resistance layer can be applied directly as a film layer onto a carrier layer or onto a container wall region to be heated, preferably imprinted such that it then realizes the desired resistance layer in the dried state. Analogously to this, the not necessarily, but preferably flexible, feed lines can be formed by a paint or ink which comprises a current-guiding function, is electrically conductive and preferably comprises silver. Here too, it is provided in a preferred manner that the feed lines are applied, preferably imprinted and dried, directly onto a carrier layer or onto a container wall region to be heated. The definition ink or paint is to be understood here in a broad sense and here includes any substance which can be applied in the manner of an ink or paint and then realizes the resistance layer or the feed lines in the dried state.

The feed lines, which realize the electrical contact device or form a constituent part of the electrical contact device, can be at least in part a constituent part of the electrical heating element and/or at least in part a constituent part of the electrical connection element. This means that the feed lines, on the one hand, can be entirely a constituent part of the at least one electrical heating element and can then be connected directly or by means of contact elements to connection contacts of the electrical connection element. As an alternative to this, the feed lines can, however, also be entirely a constituent part of the electrical connection element and can then be connected directly or by means of contact elements to the resistance layer. As a further alternative to this, the feed lines can also be realized such that part of the feed lines is a constituent part of the electrical resistance element and a further part of the feed lines is a constituent part of the electrical connection element, which are then connectable to one another either directly or by means of contact elements.

According to a particularly preferred specific embodiment, the container comprises a support, which is preferably realized integrally and/or in a plate-shaped manner and/or with two sides from a heat conducting material and comprises an inside part region, which is assigned to the capillary element region of the capillary element to be heated and consequently to the interior of the container, on which the capillary element region to be heated rests and/or is fastened in a capillary element support region, preferably rests and/or is fastened directly for heat conducting thermal contact. The support further comprises an outer part region which is remote from the inside capillary element support region and is consequently assigned to the outside region of the container, on which the electrical heating element is arranged and/or fastened for heat conducting thermal contact, wherein it is provided in a preferred manner that a carrier layer of the electrical heating element is connected to the support as a result of lamination.

According to a further particularly preferred variant, the container can comprise a projection which preferably juts out in a plateau-like manner and, for producing the electrical connection between the electrical heating element and the electrical connection element by means of the electrical contact device, engages in a receiving element of the electrical connection element, wherein it is provided in a preferred manner that feed lines on the heating element side are connectable in an electrically conductive manner, preferably by way of said assigned contact elements, to connection contacts which open out into the receiving element. Along with a functionally reliable design, this also ensures, above all, a compact design which can be manufactured in a simple manner.

In conjunction with the design just depicted, it is additionally particularly advantageous to a functionally-integrated solution when the outer part region of the support together with the electrical heating element assigned thereto form a constituent part of the projection, wherein it is provided in a preferred manner that the projection, in the mounted state, is received in the receiving element of the electrical connection element in a manner adapted to its shape and contour.

Particularly good results can also be obtained with a compact design where the capillary element, when viewed in the direction of the vertical axis, rests from above on the capillary element support region of the inside part region of the support by way of an underside of a free end region, which realizes the substance dispensing region, preferably an underside of an L leg of a capillary element which comprises an L-shaped form overall. The free end region of the capillary element is assigned to at least one container outlet opening with its top side, preferably in such a manner that it directly adjoins at least one container outlet opening, as a result of which it is possible to dispense the substance in a functionally reliable manner via the container outlet opening.

According to a particularly advantageous realization variant, the holding device can comprise, for example, a sliding and/or plug connection, where a container-side web engages in a guide slot of the electrical connection element, wherein, with the container in the slid-in and/or plugged-in state, the electrical contact device of the at least one electrical heating element is connected electrically to the electrical connection element. Such a sliding and/or plug connection is distinguished by a high level of functional reliability and allows the container to be held in a simple and reliable manner on the electrical connection element.

According to a further particularly advantageous design, the holding device comprises a housing region or realizes such a housing region which covers the container at least in the region of a container outlet opening, wherein at least one housing-side outlet opening is realized in the coverage region. In the case of said realization variant of the holding device, said holding device, in a dual function, consequently also simultaneously realizes a slim housing, above which the substance to be dispensed is able to vaporize into the surrounding area.

According to a specific design to this end, the guide slot on the housing can be formed by two individual slots which extend in each case in the slide-in direction into two parallel housing walls which are spaced apart from one another transversely to the slide-in direction. As a result, a compact, less large design, which is additionally particularly simple to manufacture, is produced overall.

The container-side web can be formed, in principle, in different ways. In a particularly preferred manner, the container-side web is formed by a flange which extends around the container at least in regions and which, once again in a dual function, can also serve for fixing a cap or a cover, as will be explained in more detail below.

For all realization variants described in detail beforehand, the capillary element, in particular a wick as capillary element, could, in principle, project beyond the container by way of a free end so that said free end realizes a substance dispensing region which lies outside the container. The solution according to the invention, however, makes it possible, in particular, to arrange the capillary element entirely in the interior of the container. In the case of such an embodiment, the capillary element then adjoins at least one container-side outlet opening by way of its free end from the inside, with a defined, preferably extremely small, gap clearance or directly, and is dispensed or vaporized from the container via the at least one container-side outlet opening to the substance. According to such a particularly preferred design, it can then be provided that the at least one capillary element adjoins a container outlet opening by way of its substance dispensing region, preferably by way of a free end region as substance dispensing region, in particular directly, so that the substance to be dispensed is conveyable by means of the capillary element in the direction of the container outlet opening and there is dispensable from the container via the at least one container outlet opening.

It is provided in a particularly preferred manner in conjunction with such a design that the at least one electrical heating element, which forms a constituent part of the container, is assigned to the substance dispensing region of the capillary element adjoining the container outlet opening in order to accelerate the vaporizing of the substance there and to increase the quantity dispensed.

The optional designs below are also advantageous to all the realization variants described beforehand:

Firstly, a design where the container, when viewed in the direction of the vertical axis, comprises an upper covering wall in which at least one container outlet opening is realized. Particularly preferred, in this connection, is a design where the at least one container outlet opening is realized in a covering-side receiving element in which the free end region of the capillary element is received, preferably in a manner adapted to its shape and/or contour. This is preferably effected in such a manner that the free end region of the capillary element directly adjoins the container outlet opening.

The at least one container outlet opening is additionally closed preferably by way of an openable cover, said openable cover being formed in a preferred manner by a tear-off film. This ensures that the substance can only be dispensed or vaporized from the container once the cover has been removed.

In principle, the entire container including the covering wall can be realized in the same material and in one piece and, in this case, the capillary element and/or the electrical heating element can be integrated into the container during the production process. However, particularly preferred is a design where the container is realized as a container which is open on one side, the covering wall of which is formed by a cap, which realizes a separate component and constituent part of the container and closes the container, wherein the at least one container outlet opening is realized in the cap. Such a container can be provided with the capillary element in a particularly simple manner, the covering wall in the form of a cap being able to be connected to the container in a simple manner as a result, for example, of integral molding or welding.

The container itself is produced, for example, by means of thermoforming or is produced from a plastics material and in a preferred manner comprises an elongated, in particular box-like, shape. In this context, such a form where the container is realized so as to be rectangular in cross section is particularly advantageous.

As has already been stated many times previously, the capillary element is formed in a preferred manner by a wick, by way of which the substance to be dispensed in the container can be conveyed in a particularly simple and functionally reliable manner in the direction of the substance dispensing region.

The container additionally preferably comprises at least one fixing device, by means of which the capillary element can be held in the interior of the container in an accurate position and condition.

The capillary element, which is formed in particular by a wick, can comprise, in principle, any suitable form. Particularly preferred, in particular in conjunction with an elongated container, however, is a capillary element which comprises an L-shaped form, with a first L leg, which extends in the interior of the container in the direction of the container vertical axis, and with a second L leg which projects therefrom at an angle and is assigned to a container outlet opening. Such a capillary element which comprises an L-shaped form has the advantage that the angled second L leg can be assigned in a particularly simple and functionally reliable manner to the at least one electrical heating element in order to be acted upon with heat by said heating element in the previously described manner on account of heat conduction, whilst the first L leg, which connects to the second L leg, extends preferably over the entire height of the container in order to convey the substance into the region of the second L leg which is acted upon with heat in the manner previously described.

Particularly preferred is additionally a specific design where the fixing device is formed by at least one of the following measures:

the first L leg, when seen in the transverse direction of the container, is held by inside wall-side projections which are located on opposite sides of the first L leg, the first L leg and/or the second L leg, when seen at the bottom of the container, is or are held between a front wall and a rear wall of the container, in particular is or are held between a rear wall and at least one front wall-side projection, the second L leg engages behind an inside wall-side projection, in particular a projection which realizes an indentation on the outside wall for receiving the at least one electrical heating element, or a projection which is formed by an inside part region of a support surface for the electrical heating element, the first L leg, when seen in the direction of the vertical axis, is supported on oppositely situated container walls.

A particularly reliable, positionally-accurate bearing arrangement of the capillary element in the interior of the container is achieved with at least one, preferably, however, with multiple or all the features just mentioned, the named measures additionally being producible in a particularly simple manner or being formed by components which are already present in any case.

According to a further particularly preferred design, the electrical connection element, preferably a holding device of the electrical connection element, comprises a decorative element which is releasably or non-releasably connected to the same, which, when viewed from a visible side of the device, conceals the container in the mounted state thereof at least in regions. Such a decorative element serves as an ornament and can be formed, for example, by a decorative cover and/or a decorative plate. Particularly preferred is a device where multiple such decorative elements are present in order to impart an individual aesthetic form to the device, for example depending on customer requirements or depending on the active agent vaporized.

Additionally claimed is a container for receiving volatile substances, in particular for receiving fragrances and/or active agents and/or for use in a device as has been appreciated beforehand in detail. Said container comprises at least one capillary element which is arranged in the container and is in contact with the substance to be dispensed and conveys it by means of capillary action to at least one substance dispensing region. Provided according to the invention is at least one electrical heating element (preferably at least one electrical heating element which adjoins the at least one capillary element) which is a constituent part of the container. For supplying power, the at least one electrical heating element can be releasably and electrically connectable, in this connection, for example by means of an electrical contact device, to the electrical connection element which is also releasably connectable to the container. Further advantageous designs of such a container have already been explained previously in detail in conjunction with the appreciation of the device according to the invention. Reference is made in this respect to the previously made statements to avoid repetition.

The advantageous realizations and further developments of the invention explained previously and/or reproduced in the subclaims can be used, in this case,—apart from, for example, in cases of clear dependencies or incompatible alternatives—individually or, however, also in arbitrary combinations with one another.

The invention and its advantageous realizations and further developments are explained in more detail below by way of simply exemplary and schematic drawings, in which:

BRIEF DESCRIPTION OF THE FIGURES

FIG. 6 shows a schematic representation of a sectional view through the container of FIGS. 1 to 5, FIG. 7 shows a schematic representation of a section along the line A-A of FIG. 6, FIG. 8 shows a schematic representation of a section along the line B-B of FIG. 6, FIG. 9 shows the electrical resistance element together with an electrical contacting device prior to insertion into the receiving element or indentation, FIG. 10 shows a view of the electrical resistance element of FIG. 9 turned through 90°, FIG. 16 shows the device according to FIG. 14 with the decorative plate removed, FIG. 21 shows a bottom view of the electrical resistance element, FIG. 26 shows a representation corresponding to FIG. 25 with the container in the assembled state and with an electrical connection element in cross section and FIG. 27 shows a representation corresponding to the cross-sectional representation in FIG. 26 in the fully mounted state.

DETAILED DESCRIPTION OF THE INVENTION

FIGS. 1 to 13 show a first exemplary embodiment of a device 1 for dispensing, in particular for vaporizing, volatile substances, such as for example fragrances and/or active agents.

Figure 1:
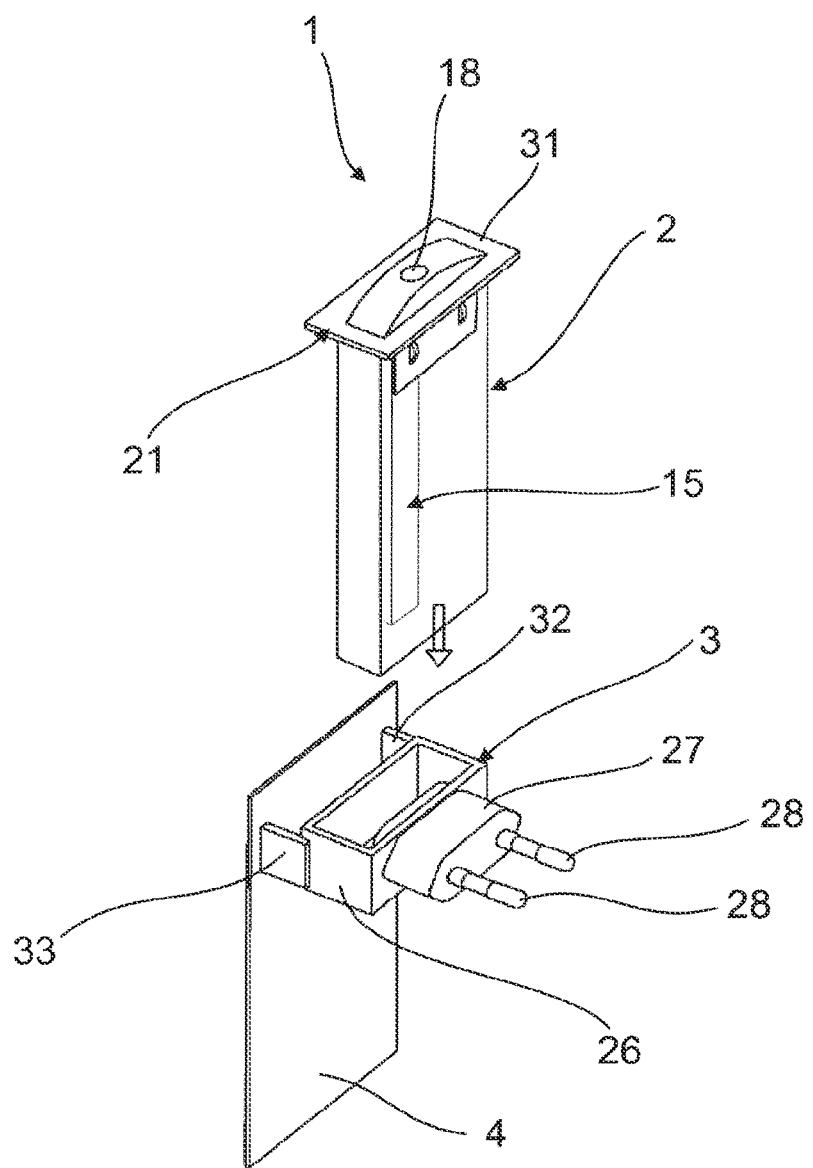
FIG. 1 shows a schematic representation in perspective of an exploded drawing of a first realization variant of a device according to the invention.

As can be seen, in particular, in FIG. 1, the device here comprises a container 2 which is releasably connectable, in a manner to be described in more detail, to an electrical connection element, on which is additionally arranged a decorative plate 4 which covers or conceals the container 2 together with the electrical connection element 3 from the visible side.

The decorative plate 4 is also releasably connected in a preferred manner to the electrical connection element 3.

As can now be seen, in particular, in FIGS. 2 to 10, the electrical heating element, which is formed here by an electrical resistance element 5, is a constituent part of the container 2. The resistance element 5, which preferably realizes a PTC resistor, as can be seen in particular in FIG. 2 and FIG. 3, in a preferred manner comprises a flat, pill-like or disk-like form and is received in a manner adapted to its shape and contour in a receiving element 7 or indentation realized in the outside wall 6 of the container 2, such that, in said heat transfer region 8, the electrical resistance element 5 abuts directly against the outside wall 6 of the container 2 in a bearing connection.

The container 2 is produced, at least in said heat transfer region 8, from a heat-conducting material, preferably a plastics material. Such a plastics material makes it possible, for example, to produce the container by means of thermoforming.

The receiving element 7 consequently forms here a container-side holder in which the resistance element 5 is able to be received in a manner adapted to its shape and contour, the electrical resistance element 5 additionally comprising another electrical contact device 9, by means of which the electrical resistance element can be releasably and electrically connected, in a manner yet to be described, to the electrical connection element 3 which is also releasably connectable to the container 2.

Figure 3:
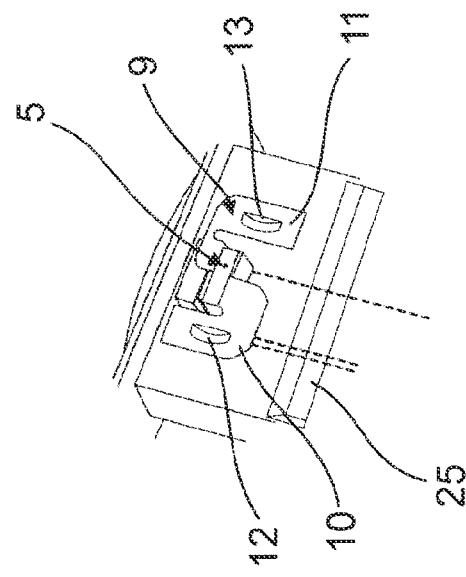
FIG. 3 shows a representation corresponding to FIG. 2 with an electrical contact device of the resistance element.

As can be seen in particular in FIG. 3 in conjunction with FIG. 10, the electrical contact device 9 of the electrical resistance element 5 comprises here, as an example, two flat, plate-shaped contact regions 10, 11, which extend substantially parallel to the outside wall 6 of the container 2 or are arranged or rest on the outside wall 6 of the container and each comprise, in turn, raised contact elements in the form of contact pins 12, 13. As can be seen from the figures, the term "contact pin" is to be understood here in the broadest sense and is also consequently to include the contact elevations shown in the figures.

Figure 11:
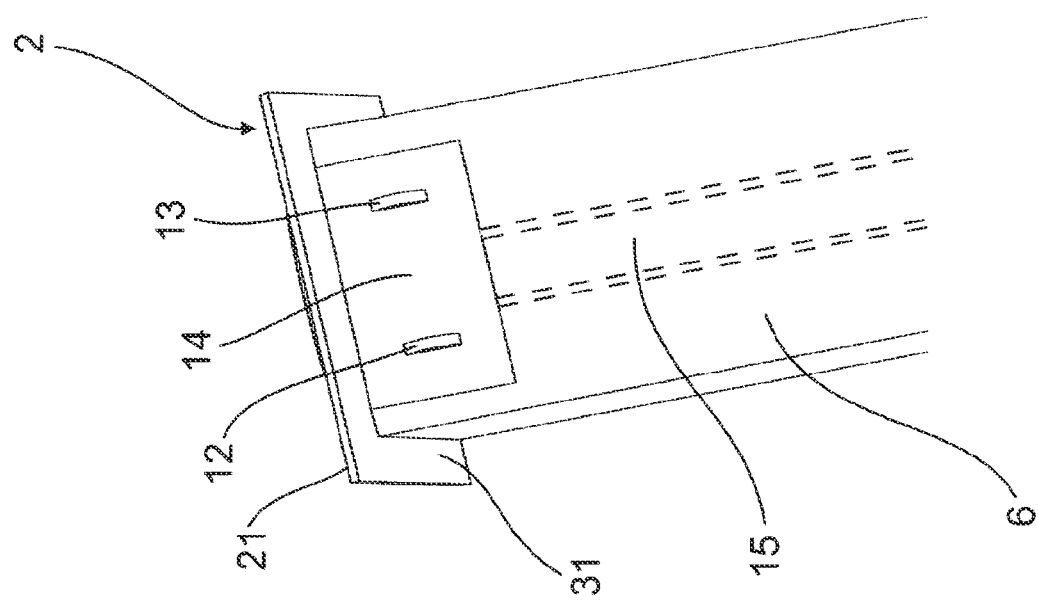
FIG. 11 shows the container together with an electrical heating or resistance element which is provided with a cover on the contact region.

As can be seen in FIG. 11, the contact regions 10, 11 of the electrical contact device 9 of the electrical resistance element 5 are provided in a preferred manner with a cover 14, which covers the contact regions 10, 11 entirely, can be realized, for example, in the form of a cover film and through which the contact pins 12, 13 project for connection to the electrical connection element 3.

The cover 14 is releasably mounted, for example, on the contact regions 10, 11 and can be used, for example, for labelling or for marking the container.

It is obvious that the cover 14, if it is not removed or is not to be removed, is realized in a thermally stable manner in order not to be damaged in a heating operation.

As can be seen in particular in FIG. 6, a capillary element 15, realized for example by a wick, is held in the interior of the container 2, which capillary element, as an example, has an L-shaped form here with a first L leg 16 which, when viewed in the direction of the vertical axis of the container 2, extends substantially over the entire container length, for example from the bottom region to the top region. In addition, the capillary element comprises here a second L leg 17 which projects at an angle from the first L leg and realizes a substance dispensing region which substantially directly adjoins a container outlet opening 18 so that the substance to be dispensed, received in the container 2, is conveyable by means of the capillary element 15 in the direction of the container outlet opening 18 and there can be dispensed out of the container 2 via the container outlet opening 18.

The second L leg 17 consequently realizes here both a free end region of the capillary element 15 and a substance dispensing region, the electrical resistance element 5 being assigned here to the second L leg, which adjoins the container outlet opening 18, as the substance dispensing region of the capillary element. The capillary element 15 specifically encompasses here the region of the receiving element 7 in the transition region from the first L leg to the second L leg such that the capillary element region to be heated rests or abuts there in a bearing connection.

Said direct or gap-free abutment of the capillary element 15 against the inside wall 19 of the container and consequently in the heat transfer region 8 ensures that the heat is transferred by means of heat conduction from the electrical resistance element via the container wall in the heat transfer region 8 directly to the capillary element 15, as a result of which a high substance dispensing rate is obtained via the container outlet opening 18 even at relatively low temperatures.

As can be seen in particular from FIGS. 6 and 7, the container outlet opening 18 is closed by way of an openable cover 20 which can be formed, for example, by a tear-off film. If this is removed (FIG. 7), the substance is then able to escape or vaporize via the container outlet opening 18.

The container 2 is realized here in a preferred manner as a container that is open on one side, the covering wall of which is formed by a cap 21 which forms a separate component and constituent part of the container, closes the container 2 and is, for example, welded fixedly to the container 2. The container outlet opening 18 is then realized in said cap 21 as the covering wall.

As can be seen in FIG. 1 in conjunction with FIGS. 6, 7 and 8, the container, which is produced in a preferred manner from plastics material, comprises here an elongated, box-like form with a substantially rectangular cross section.

Figure 4:
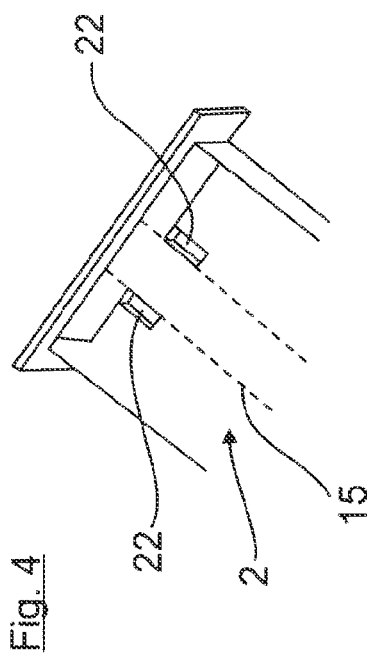
FIG. 4 shows a rear view of FIG. 2 and FIG. 3 turned through 180° with inside wall-side projections for holding a wick.

The capillary element 15, which is preferably formed by a wick, can be held and fixed in a simple manner in such a container 2. There are various possibilities for this purpose which are listed below simply as examples:

the first L leg 16, when seen in the transverse direction of the container 2, can thus be held, for example, by inside wall-side projections 22 which are located on opposite sides of said first L leg (FIG. 4).

Furthermore, as can be seen in particular in FIG. 6, the first L leg 16 and/or the second L leg 17, when seen at the bottom of the container 2, is or are held between a front wall 23 and a rear wall 24 of the container 2, to which end, for example, front wall-side projections can also be provided such as, for example, the receiving element 7 which supports the capillary element 15 in an upper region in the direction of the vertical axis, and a lower projection 25, in this connection, which holds the first L leg 16 in a lower region, in this connection, between the front wall 23 and the rear wall 24.

As an alternative to this, but which is, however, not shown here, the first L leg 16, when seen in the direction of the vertical axis, can also be supported on the oppositely situated container walls, that is to say on the covering wall and the bottom wall.

Figure 5:
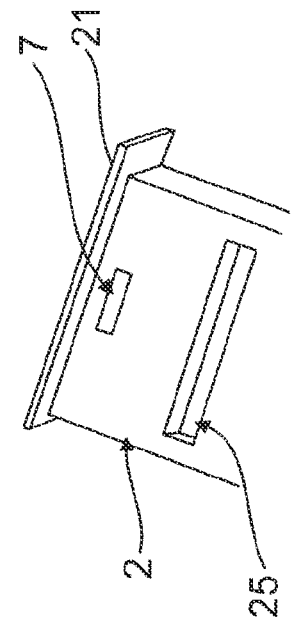
FIG. 5 shows a front view corresponding to FIG. 2 and FIG. 3, where the receiving element or indentation for receiving the resistance element is shown along with a front wall-side indentation for fixing the wick in position in the interior of the container.
Figure 2:
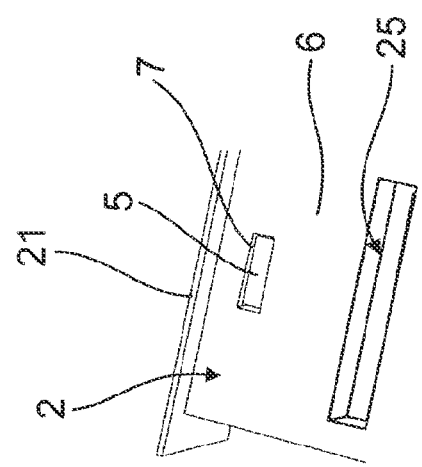
FIG. 2 shows a schematic representation of a view of a detail with a resistance element received in a container wall-side receiving element or indentation.

The lower projection 25 can also be seen in FIG. 5.

Figure 12:
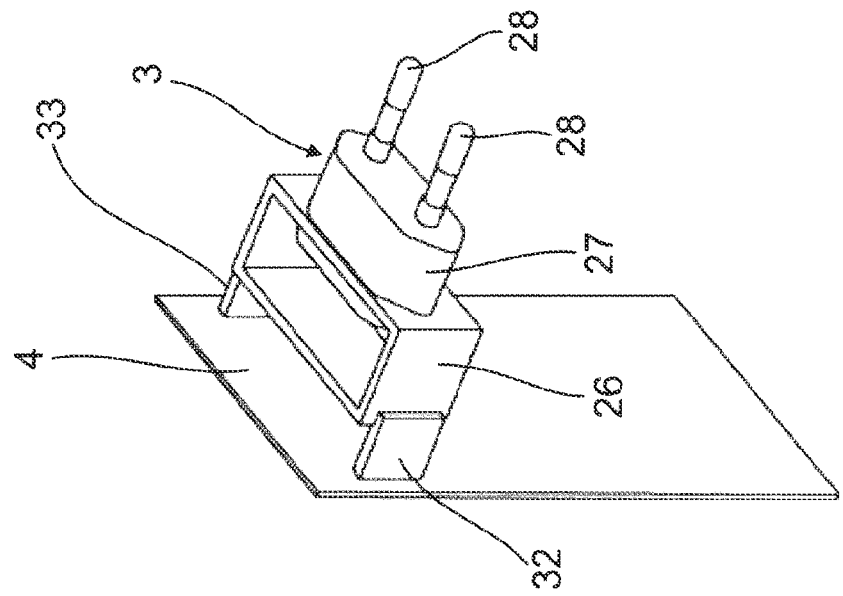
FIG. 12 shows an enlarged representation of the electrical connection element together with a decorative plate.
Figure 13:
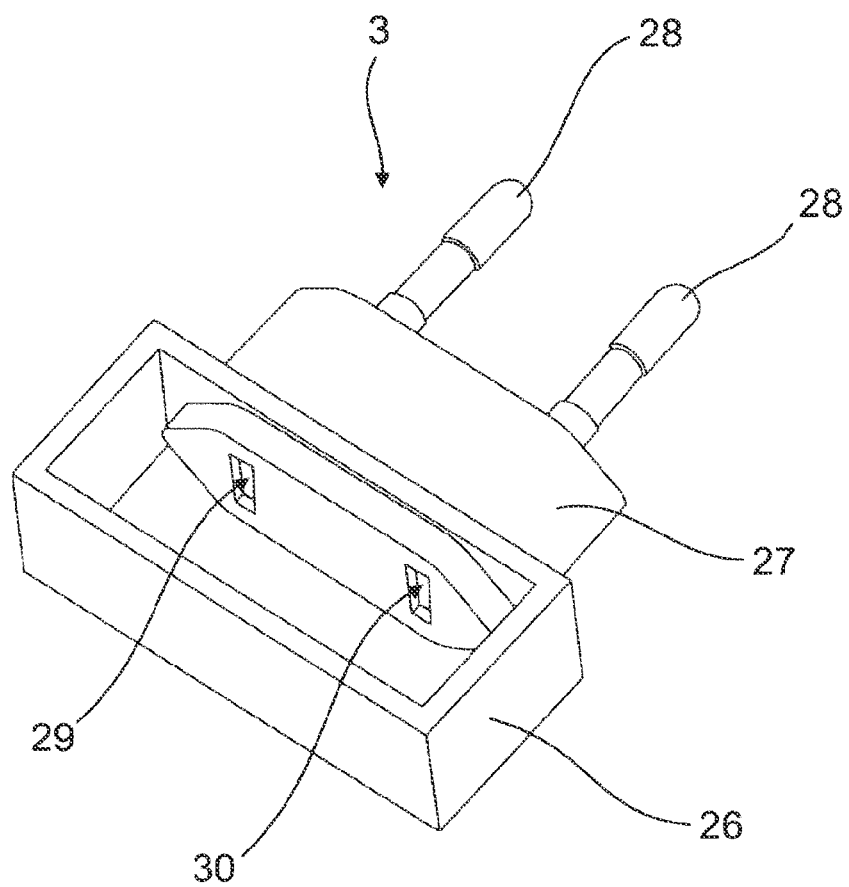
FIG. 13 shows a perspective top view of the electrical connection element.

As can be seen in particular from the overall view in FIGS. 1, 12 and 13, the electrical connection element 3 comprises a holding device which is formed here purely as an example by a holding ring 26, by means of which the container 2 can be mounted on the electrical connection element in the region of the electrical resistance element 5.

The electrical element 3 specifically comprises here a conventionally designed plug 27 with contact pins 28 for connection to an electrical socket, the holding ring 26 connecting directly to said plug 27. In a preferred manner, the holding ring 26 is integrally molded on the plug 27 so that the electrical connection element 3, for example according to a preferred design, is a one-part component which can be produced, for example, by injection molding.

The holding ring 26 encompasses the container, which is inserted into the holding ring 26, in the mounted state in a preferred manner such that the holding ring 26 abuts against the container outside wall at least in regions.

As can be seen in particular from FIG. 13, recesses 29, 30, which are assigned to the contact pins 12, 13 of the electrical resistance element 5 arranged on the container 2, are provided in the region of the holding ring 26, in which recesses the contact pins 12, 13 project or engage in the mounted state preferably in a positive locking and/or latching locking manner in order to be connected in an electrically conductive manner to connection contacts of the electrical connection element 3 which open out there.

In order to ensure that the raised contact pins 12, 13 are able to latch in the recesses 29, 30 of the holding ring 26, it is provided according to a particularly preferred design that the holding ring is elastically flexible at least in regions so that said holding ring 26, when the container is inserted into the holding ring 26 causing the contact pins 12, 13 to abut against the inside wall region of the holding ring 26 surrounding the recesses 29, 30, extends elastically at least in regions until the contact pins 12, 13 are in an engagement position at the level of the recesses 29, 30 in which engagement position the extended wall region of the holding ring 26 then springs back again to produce a positive locking connection. In an analogous manner, during removal, the contact pins 12, 13 move out of engagement with the recesses 29, 30 and as a result the contact pins 12, 13, in turn, move into abutment against the inside wall region of the holding ring 26 surrounding the recesses 29, 30, as a result of which said holding ring extends elastically and the container 2 is able to be disengaged from the holding ring 26.

As can be seen further, for example, in FIG. 1, the container 2, preferably in the region close to the cap, comprises a flange 31 as a stop element which extends around at least in regions, here completely, and is realized such that when the flange 31 rests on the top side of the holding ring 26, when seen in the direction of the vertical axis, the contact pins 12, 13 of the electrical resistance element 5 coincide with the recesses 29, 30 in the holding ring in order to produce the releasable electrical connection between the electrical resistance element 5 and the electrical connection element 3.

In the first realization variant shown here as an example, the releasable connection between the container 2 and the electrical connection element 3 is consequently formed on one hand via the contact pins 12, 13 of the electrical contact device 9 of the electrical resistance element 5 arranged on the container 2. Said releasable connection between container 2 and electrical connection element 3 is additionally supported by the releasable arrangement of the container 2 in the holding ring 26 of the electrical connection element 3, which brings about, in particular, a positionally accurate alignment of the contact pins 12, 13 with reference to the connection contacts of the electrical connection element 3 which open out into the recesses 29, 30.

Figure 15:
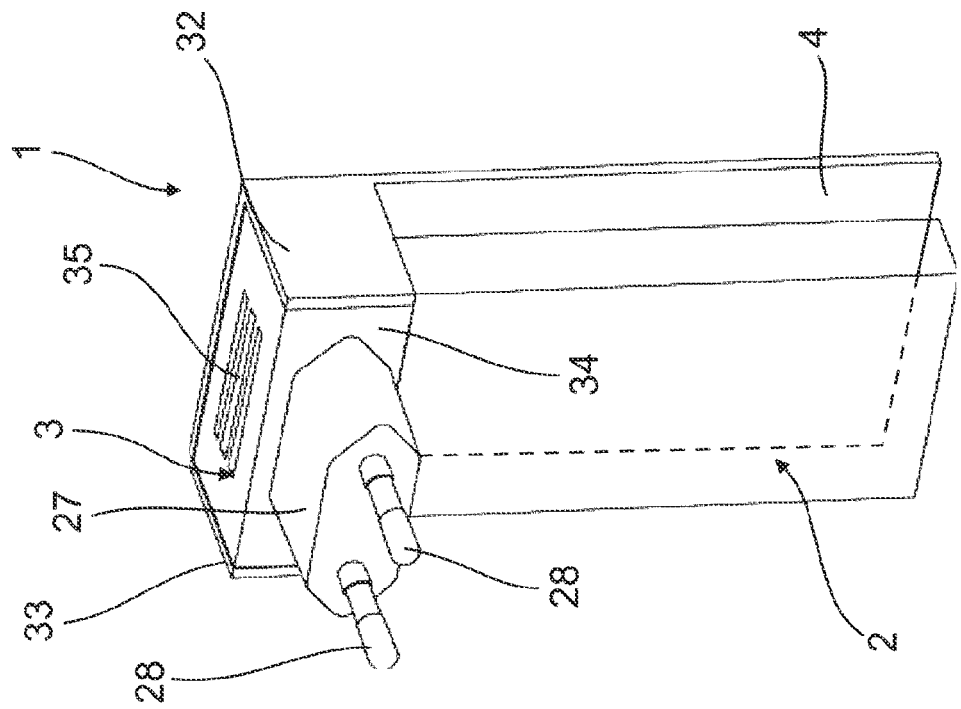
FIG. 15 shows a rear view of the representation in FIG. 14.
Figure 14:
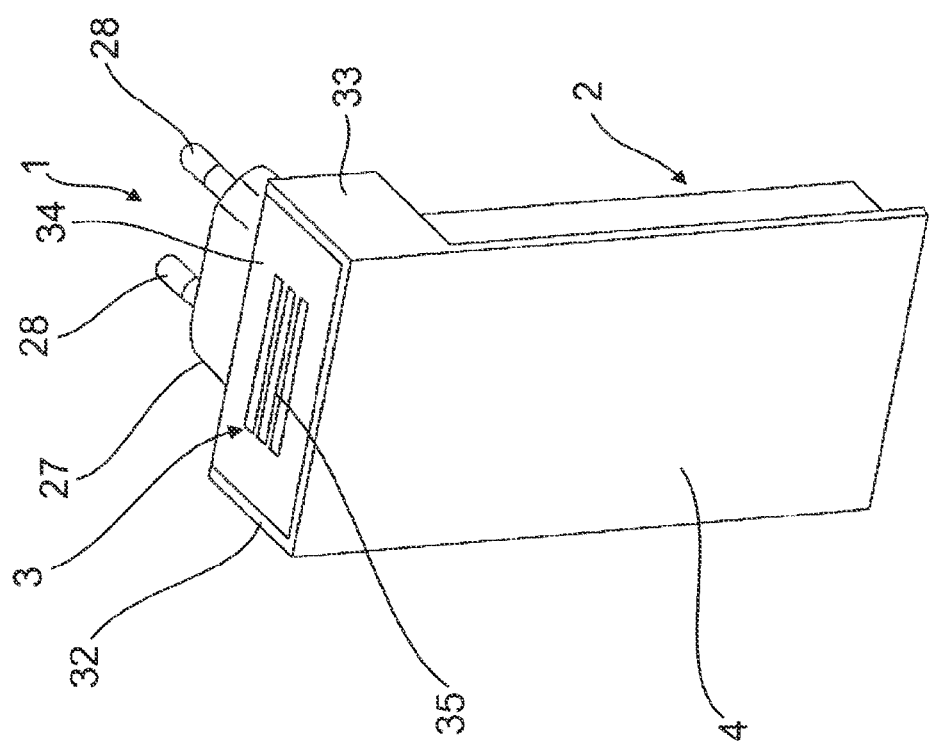
FIG. 14 shows a schematic front view in perspective of a second realization variant of the present inventive concept.

A second realization variant of a solution according to the invention is now explained in more detail below with reference to FIGS. 14 to 27:

In the case of said second exemplary realization variant according to the invention, identical components are designated with identical reference symbols and, as can be seen in FIGS. 14 to 16, the device 1 is also designed in principle with three parts so that it includes a container 2, an electrical connection element 3 and a decorative plate 4 which is releasably fixable on the electrical connection element 3. Said decorative plate 4, as can be seen in particular in FIG. 14, covers the container in the mounted state from the visible side so that it is not visible or is only visible in part.

To fix the decorative plate, it can encompass the electrical connection element 3 laterally, just as in the first embodiment, with two holding brackets 32, 33 which project laterally from said decorative plate and are fixed there by means of a releasable connection (not shown here), for example by means of a latching and/or clip connection. In the case of the previously described first realization variant, the holding brackets 32, 33 cooperate with the holding ring 26 and in the case of the second realization variant described below, with a housing region 34 of the electrical connection element, which housing region 34 is attached, in particular integrally molded, to the plug 27 and realizes a slim housing part which covers the container 2, as shown in FIGS. 14 to 16, in the region of its container outlet opening 18, multiple housing-side outlet openings 35, here in the form of slots simply as an example, being realized here as an example in the coverage region, via which outlet openings the substance to be dispensed is able to vaporize out of the housing region 34 (see also arrows 36 in FIG. 27).

Figure 18:
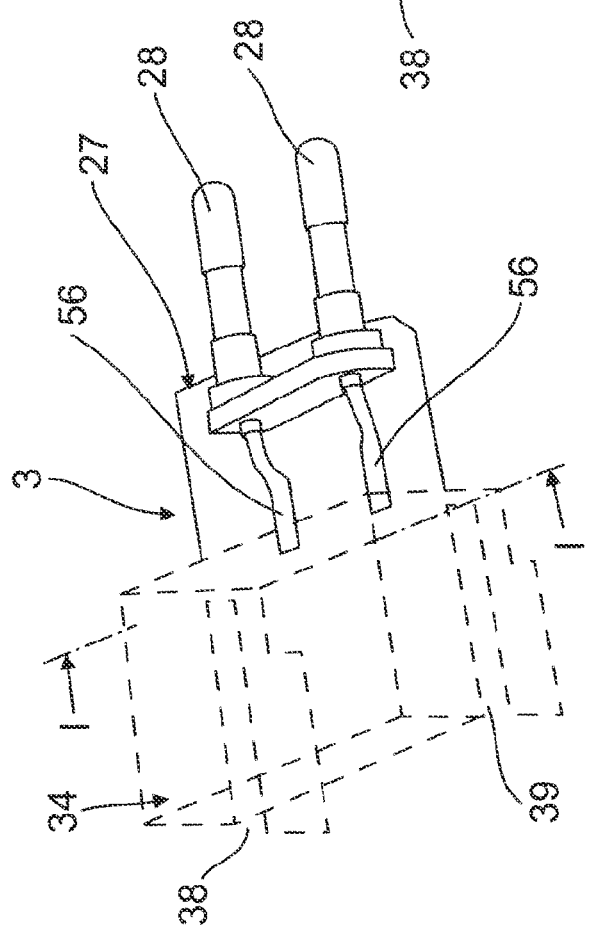
FIG. 18 shows a schematic representation in perspective of a schematic diagram of the electrical connection element together with the connection contacts which are coupled with a plug.
Figure 26:
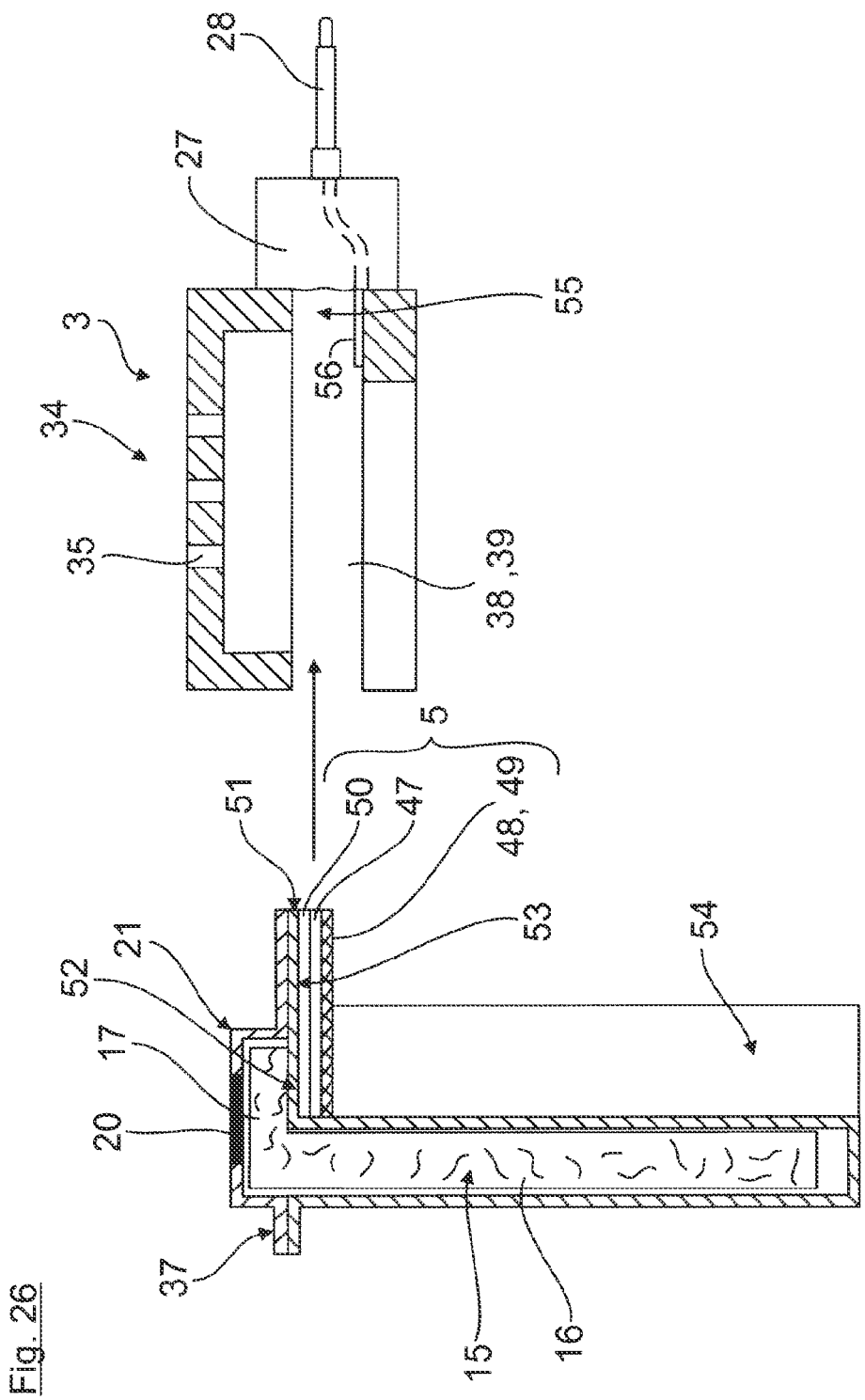

As can also be seen additionally from FIG. 16 in conjunction with FIG. 18 and FIGS. 26 and 27, the housing region 34 here additionally also realizes the holding device for the container 2, said holding device being formed or realized specifically by a sliding and/or plug connection, where a container-side web 37, which is formed here as an example by a flange which extends around the container 2, by way of web regions 43, 44, which are oppositely situated transversely to the insertion direction, engages in a manner that is adapted substantially to its form and contour in two individual slots 38, 39 which each extend in the insertion direction into two parallel housing walls 40, 41 which are also spaced apart from one another transversely to the insertion direction.

The individual slots 38, 39, which realize a guide slot of the sliding and/or plug connection, are realized, in this connection, in conjunction with the container-side web 37 such that in the mounted state an electrical contact device 9, which is to be described in more detail, of an electrical heating element is connected electrically to the electrical connection element 3.

Figure 17:
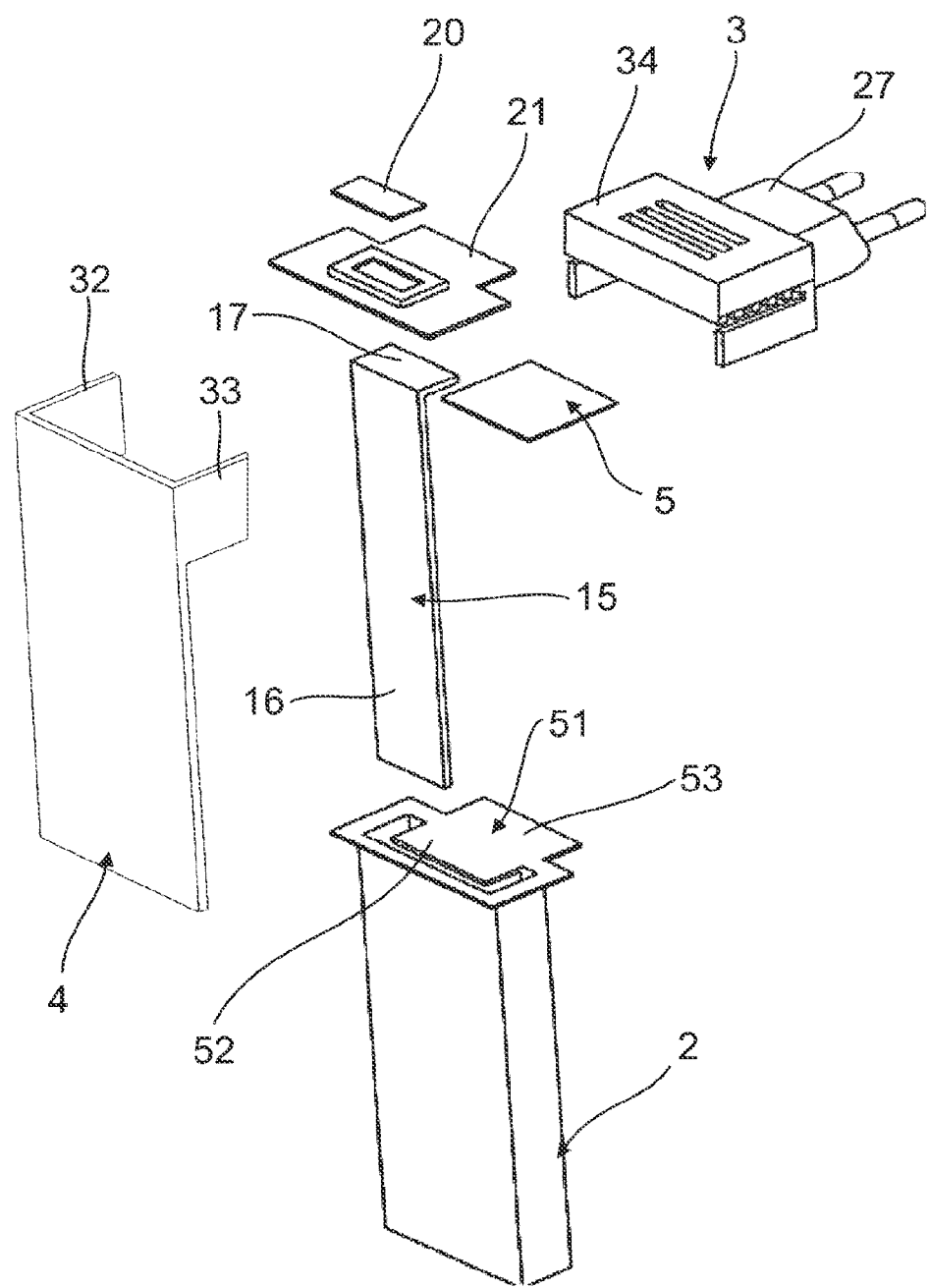
FIG. 17 shows a schematic representation in perspective of an exploded drawing of the individual parts of the device according to the second realization variant.
Figure 19:
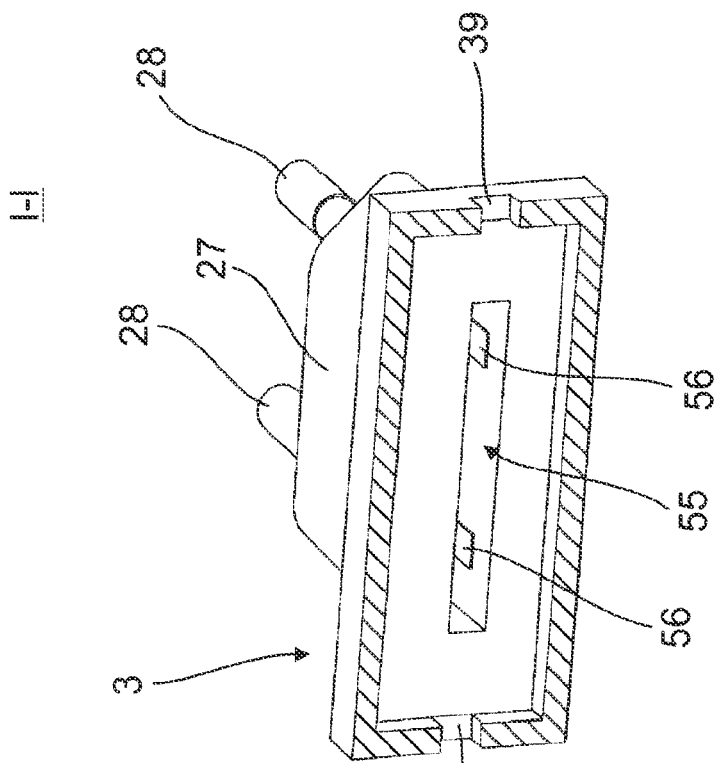
FIG. 19 shows a section along the line H of FIG. 18, FIG. 20a, b show a schematic representation in perspective of the container together with an electrical heating or resistance element.
Figure 25:
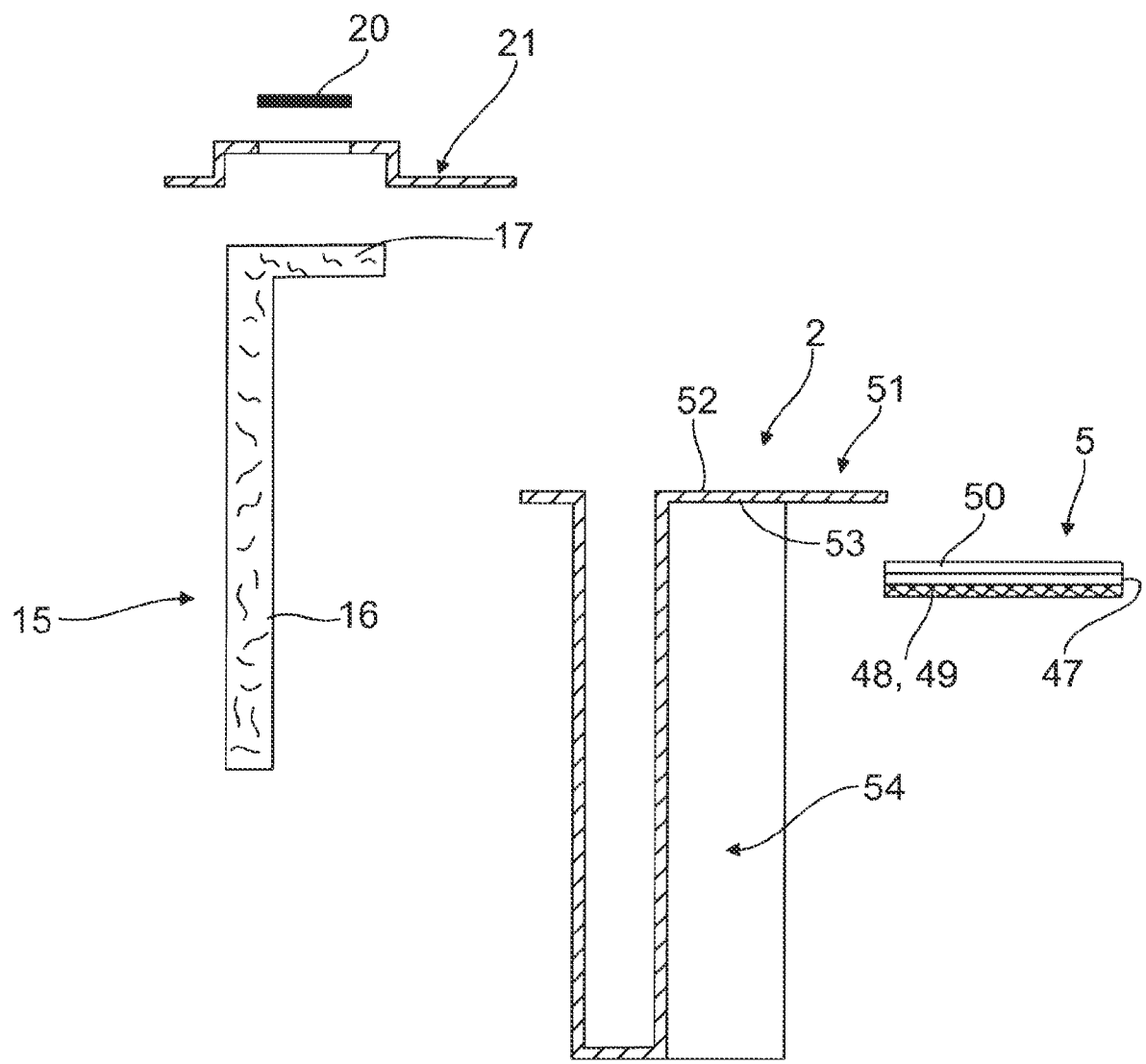
FIG. 25 shows a schematic representation of an exploded drawing of a cross section through the container.

As can be seen further in particular from the exploded representations of FIGS. 17 and 25, the container 2 here is realized once again as an example as an upwardly open container which is closable with a cap 21 as the covering wall.

Figure 23:
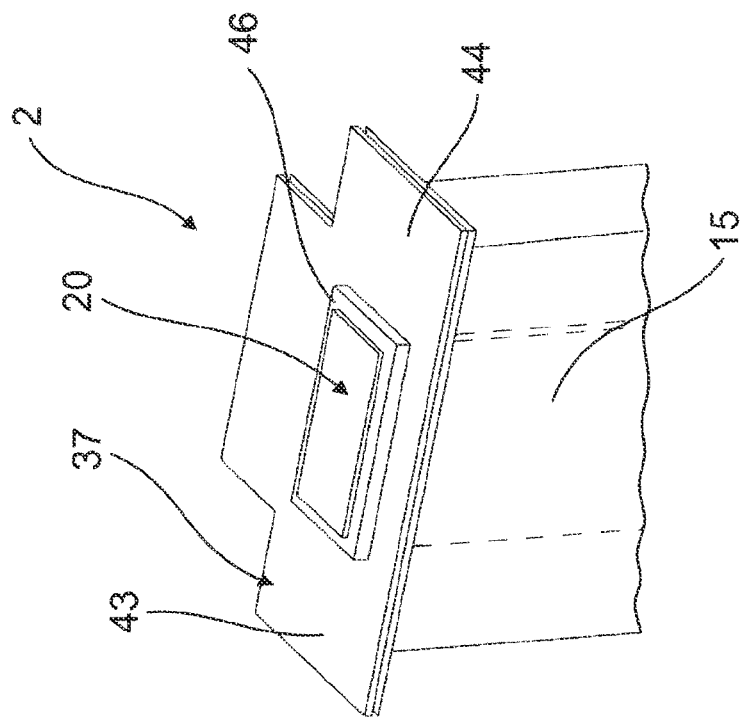
FIG. 23 shows a schematic representation of a top view of the top side of the container with the container outlet opening open.
Figure 24:
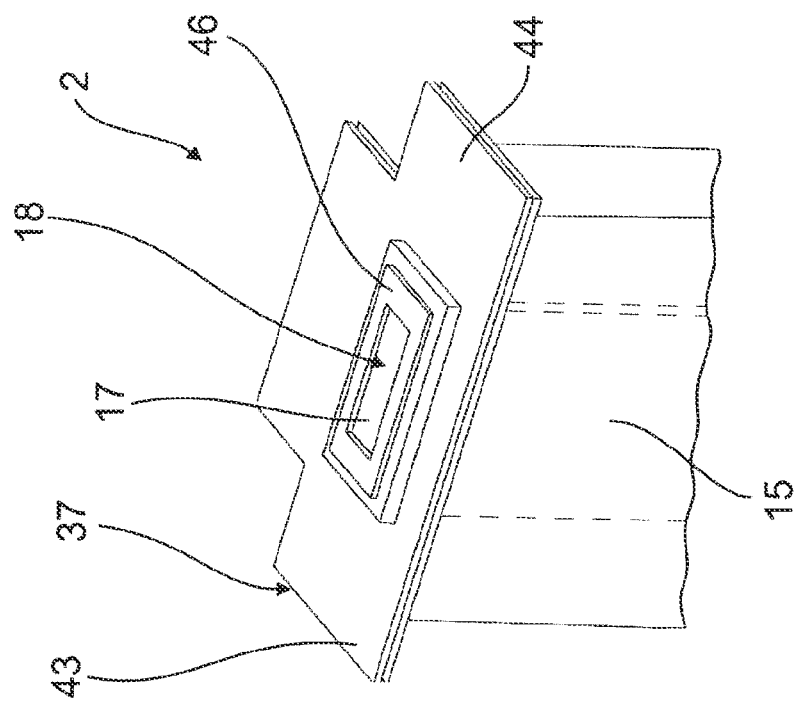
FIG. 24 shows the container according to FIG. 23, where the container outlet opening is closed with a cover in the form of a tear-off film.

As can also be seen further in particular in FIGS. 23 and 24, a container outlet opening 18, which is closable with a cover 20 analogously to the first realization variant, is once again provided in the cap 21 and is formed, for example, by a tear-off film or the like. If said tear-off film or cover 20 is removed (the state in FIG. 23), then the substance is able to escape or vaporize out of the container interior via the container outlet opening 18.

As can be seen further from FIGS. 23 and 24, the cap 21 as a constituent part of the container 2 also realizes here the oppositely situated web regions 43, 44 of the web 37 which, with the container in the mounted state, engage in the individual slots 38, 39 of the housing walls 40, 41. The web regions 43, 44 and the individual slots 38, 39 are dimensioned in this connection such that the web regions 43, 44 are held releasably in the individual slots 38, 39 by means of a clamping connection. As a result, reliable fixing of the container 2 on the electrical connection element 3 is achieved on the one hand and additionally, however, it is also ensured that the container 2 is able to be released again from the electrical connection element in a simple manner. As can be seen in particular in FIGS. 16 and 17, individual clamping projections 45 can also be realized for this purpose in the region of the individual slots 38, 39.

A capillary element 15, which in a preferred manner is L-shaped and in a preferred manner is formed by a wick or is produced from wick material, is arranged in the interior of the container 2.

Here too, the capillary element 15, when seen in the direction of the vertical axis of the container, once again extends with a first L leg 16 substantially over the entire container length to directly below the container outlet opening 18 in the cap 21, which can be seen, for example, particularly well in FIGS. 26 and 27. As a result, the second L leg 17, which realizes the substance dispensing region, directly adjoins the container outlet opening 18 or is received there at least in regions, where applicable even in a cap-side receiving element 46 in order to enable the substance to be dispensed or vaporized in a functionally reliable manner.

The fixing or holding of the capillary element 5 in the interior of the container 2 can be effected in principle analogously to the first realization by way of one or multiple of the measures described there. Reference is made here to the statements made previously in this respect.

Figure 22:
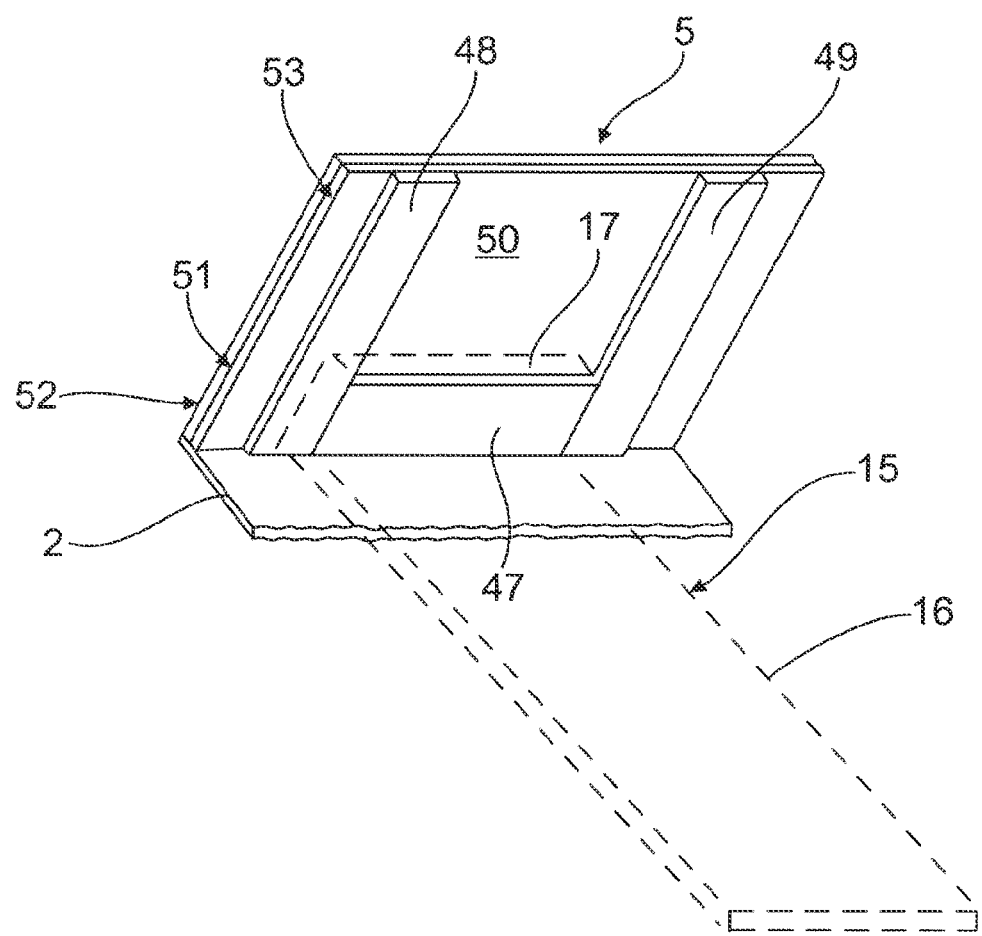
FIG. 22 shows a schematic sketch with a capillary element, the capillary element region to be heated being assigned to the layer resistance.

The essential difference between the second realization variant and the first realization variant, however, is that here the electrical heating element, which is also formed once again in a preferred manner by an electrical resistance element 5, is realized in a different manner, which is explained in more detail below as an example:

the electrical heating or resistance element 5 here comprises a resistance layer 47 as a heating layer, which can also be seen in particular in FIGS. 21 and 22, the electrical contact device 9 in the example case shown here comprising feed lines 48, 49 which are connected to said resistance layer 47. Two feed lines 48, 49, which are spaced apart from one another and comprise an electrical connection to the resistance layer 47 which lies in the space between, are specifically provided here.

In the case of said embodiment shown here, the resistance layer 47 together with the feed lines 48, 49 is specifically applied on a carrier layer 50 as a substrate which is arranged in the mounted state (see in particular FIGS. 22 and 26 also) on the outside wall of the container 2 in a flat bearing connection in a manner described in more detail below and is assigned to the capillary element region to be heated. In the example case shown here, said assignment is effected such that an underside of the second L leg 17 realizing the capillary element region to be heated is directly in direct heat-conducting thermal contact with the electrical resistance element 5.

It can be seen very well in FIG. 22 that the resistance layer 47 can be adapted here with regard to shape and size to the capillary element region to be heated (formed here by the second L leg 17 simply as an example), which is, however, not absolutely necessary. In principle, the resistance layer 47 could also extend over a larger region on the carrier layer 50.

The carrier layer 50, the resistance layer 47 and the feed lines 48, 49 are preferably realized in such a manner or produced from such a material that they realize a heating and resistance element 5 that is flexible overall.

Particularly preferred, in this connection, is a design where the, preferably flexible, resistance layer 47 is formed by an electrically conductive ink or paint which comprises a resistance function, preferably a PTC function, and is applied, preferably imprinted, onto the carrier layer 50 for example, as a film layer. The imprinting can be effected, for example, using a silk-screen printing method.

Analogously to this, the, preferably flexible, feed lines 48, 49 are formed in a preferred manner by an electrically conductive paint or ink which comprises a current-guiding function, for example a paint or ink which comprises silver. Here too, the feed lines 48, 49 can be advantageously imprinted directly onto the carrier layer 50, for example also in conjunction with a silk-screen printing method.

The carrier layer can be produced, for example, from a plastics material, for example from polyethylene terephthalate (in short PET).

As can be seen in particular from the overall view of FIGS. 17, 20 and 22, the container 2 comprises on an, when seen in the direction of the vertical axis, upper region, to which the cap 21 and/or the second L leg 17 of the capillary element is assigned, a support 51 which is realized here, for example, in an integral, plate-shaped and two-sided manner and is produced from a heat-conducting material. Said support 51 comprises an inside part region 52, which is assigned to the L leg 17 as a capillary element region to be heated of the capillary element 15 and is consequently assigned to the interior of the container 2, on which the L leg 17 directly rests and/or is fastened for heat-conducting thermal contact as a capillary element region to be heated in a capillary element support region. The support 51 further comprises an outer part region 53, which is remote from the inside capillary element support region and is consequently assigned to the outside region of the container 2, on which the electrical heating element 5 is arranged and/or fastened for heat-conducting thermal contact, in a preferred manner such that a carrier layer 50 of the electrical heating element 5 is connected to the support 51 or to the outer part region 53 by means of lamination. As shown further, a notch 54 can be realized on the container wall, assigned to the support 51 and consequently to the arrangement region of the electrical resistance element 5, said notch enabling, on the one hand, very good assignment of the electrical resistance element 5 to the support 51 and, on the other hand, also reliable fixing of the capillary element 15 in the interior of the container. Said notch 54 can extend over the entire container length (for example FIGS. 25 to 27) or, however, also only over a part region of the same (see FIG. 20 b).

The support surface 51 comprises here a substantially rectangular outside contour and corresponds as regards its size and the dimension in a preferred manner substantially to the dimensions of the flat and/or flexible electrical resistance element 5 which is mounted on said support surface 51 or on the outer part region 53 thereof.

The electrical heating element 5 can further comprise a, preferably flexible, protective layer which covers the resistance layer 47 together with the feed lines 48, 49 applied on the carrier layer 50 at least in regions, which is, however, not shown here. The only important point in this connection with reference to the feed lines 48, 49 is that they are arranged or realized such that they are able to be contacted with electrical contact elements.

As can be seen in particular in FIG. 26, the outer part region 53 of the support 51 together with the electrical heating element 5 assigned thereto forms a constituent part of a projection which projects from the container 2 and engages in a receiving element 55 of the electrical connection element 3 for producing the electrical connection between the electrical heating element 5 and the electrical connection element 3, such that the feed lines 48, 49 on the heating element side forming here a constituent part of the electrical contact device 9 are connectable in an electrically conductive manner to connection contacts 56 which open out into the receiving element 55 and also form a constituent part of the electrical contact device 9 (see FIG. 27).

The design and dimensioning of the plateau-like projection and/or of the receiving element 55 is effected in this connection in a preferred manner such that in the mounted state the projection is received in the receiving element 55 of the electrical connection element 3 in a manner that is adapted to its form and/or contour, in particular is held releasably in the receiving element 55 by means of a positive locking or clamping connection.

The electrical resistance element 5 is shown excessively thickly in particular in FIGS. 25 to 27 simply for reasons of better presentation. It is clear that the electrical resistance element 5 can obviously be realized extremely thinly.

The invention claimed is:

1. A device for dispensing volatile substances, said device comprising:
   a container for a substance to be dispensed;
   at least one capillary element arranged at least in part in said container for contacting said substance to be dispensed and for conveying said substance by capillary effect to at least one substance dispensing region;
   at least one electrical heating element adjoining said at least one capillary element, and said electrical heating element being an electrical resistance element and having a resistance layer as a heating layer which is assigned to a capillary element region to be heated and/or is film-like;
   an electrical connection element for supplying said at least one electrical heating element with electrical power, said at least one electrical heating element being a constituent part of said container, and said container being releasably connectable to said electrical connection element; and
   an electrical contact device by way of which said at least one electrical heating element is releasably and electrically connectable to said connection element;
   said resistance layer being arranged directly or indirectly with an interposition of at least one intermediate layer in a heat transfer region on an outside surface of a container wall, which is produced at least in said region from a heat conducting material, and in said heat transfer region, said capillary element region to be heated abuts against an inside surface of said container wall in a bearing connection, such that said electrical heating element transfers heat to said container wall by means of heat conduction and from there to said capillary element region to be heated;

said container having a support, which is realized integrally and/or in a plate-shaped manner and/or with two sides from a heat-conducting material and having an inside part region, which is assigned to said capillary element region of said capillary element to be heated and consequently to said interior of said container and on which said capillary element region to be heated rests and/or is fastened in a capillary element support region, and said support having an outer part region, which is remote from an inside capillary element support region and is consequently assigned to said outside region of said container and on which said electrical heating element is arranged and/or fastened for heat-conducting thermal contact.

2. The device according to claim 1, wherein said electrical contact device is at least in part a constituent part of said at least one electrical heating element and/or at least in part a constituent part of said electrical connection element.

3. The device according to claim 1, wherein said releasable connection between said container and said electrical connection element is produced in part or entirely by said electrical contact device.

4. The device according to claim 1, wherein said releasable connection between said container and said electrical connection element and/or between said at least one electrical resistance element and said electrical connection element is formed by a positive locking connection and/or by a non-positive locking connection.

5. The device according to claim 1, wherein said electrical connection element comprises a holding device, by means of which said container is held on said electrical connection element.

6. The device according to claim 1, wherein said container and/or said electrical connection element comprises at least one stop element which positions said container in a mounted state such that said at least one electrical heating element is connectable or connected electrically to said electrical connection element by means of said electrical contact device, which are arranged on said at least one electrical heating element, are assigned to connection contacts of said electrical connection element and are connectable or connected to said connection contacts so as to be electrically conductive.

7. The device according to claim 5, wherein said electrical connection element is formed by a plug which comprises said holding device, wherein said holding device is fixedly connected to said plug and/or said electrical connection element is a one-piece component which is produced by injection molding.

8. The device according to claim 5, wherein said holding device encompasses said container, at least in a region of said at least one electrical heating element.

9. The device according to claim 1, wherein said electrical contact device comprises feed lines which are connected or connectable to said resistance layer and by way of which said electrical connection between said resistance layer and said electrical connection element is producible.

10. The device according to claim 9, wherein there are two feed lines provided which are spaced apart from one another and comprise an electrical connection to said resistance layer which is located in said space between and/or in that said resistance layer realizes a PTC resistance element.

11. The device according to claim 9, wherein said electrical heating element comprises a carrier layer as substrate, on which said resistance layer is applied as a film layer and/or together with said feed lines, wherein said carrier layer and said resistance layer are realized in a flexible manner for realizing an electrical heating element which is flexible overall.

12. The device according to claim 11, wherein said carrier layer forms said at least one intermediate layer.

13. The device according to claim 12, wherein said electrical heating element further comprises a protective layer which covers, at least in regions, said resistance layer which was applied on said carrier layer.

14. The device according to claim 9, wherein said resistance layer is formed by an electrically conductive ink or paint which comprises a resistance function, wherein said resistance layer is applied as a film layer onto a carrier layer or onto a container wall region which is to be heated.

15. The device according to claim 9, wherein said feed lines are formed by a paint or ink, which comprises a current-carrying function, is electrically conductive, wherein said feed lines are applied onto a carrier layer or onto a container wall region which is to be heated.

16. The device according to claim 9, wherein said feed lines, which realize said electrical contact device or form a constituent part of said electrical contact device, are at least in part a constituent part of said electrical heating element and/or at least in part a constituent part of said electrical connection element.

17. The device according to claim 1, wherein said container comprises a projection which juts out in a plateau-like manner and, for producing said electrical connection between said electrical heating element, and said electrical connection element by means of said electrical contact device, engages in a receiving element of said electrical connection element, wherein feed lines on a heating element side are connectable in an electrically conductive manner by way of said assigned contact elements to connection contacts which open out into said receiving element.

18. The device according to claim 17, wherein said outer part region of said support together with said electrical heating element assigned thereto form a constituent part of said projection, wherein said projection, in said mounted state, is received in said receiving element of said electrical connection element in a manner adapted to its shape and/or contour.

19. The device according to claim 18, wherein:
said capillary element, when viewed in a direction of a vertical axis, rests with an underside of a free end region, which realizes said at least one substance dispensing region from above on said capillary element support region of said inside part region of said support, and
said free end region of said capillary element is assigned to at least one container outlet opening with its top side and directly adjoins at least one container outlet opening.

20. The device according to claim 5, wherein said holding device comprises a sliding and/or plug connection or is formed by a sliding and/or plug connection, where a container-side web engages in a guide slot of said electrical connection element, wherein, with said container in said slid-in and/or plugged-in state, said electrical contact device of said at least one electrical heating element is connected electrically to said electrical connection element.

21. The device according to claim 20, wherein said holding device comprises and/or realizes a housing region which covers said container at least in said region of a container outlet opening, wherein at least one housing-side outlet opening is realized in said coverage region.

22. The device according to claim 21, wherein said guide slot on said housing is formed by two individual slots which extend in each case in a slide-in direction into two parallel housing walls which are spaced apart from one another transversely to said slide-in direction.

23. The device according to claim 22, wherein said container-side web is formed by a flange which extends around said container at least in regions.

24. The device according to claim 1, wherein said at least one capillary element adjoins a container outlet opening by way of its substance dispensing region in such a manner that said substance to be dispensed is conveyable by said capillary element in a direction of said container outlet opening and is configured to be output there out of said container by means of said at least one container outlet opening, wherein said at least one electrical heating element which forms a constituent part of said container is assigned to said substance dispensing region of said capillary element which adjoins said container outlet opening.

25. The device according to claim 1, wherein said container, when viewed in a direction of a vertical axis, comprises an upper covering wall in which at least one container outlet opening is realized.

26. The device according to claim 25, wherein said at least one container outlet opening is realized in a covering-side receiving element in which a free end region of said capillary element is received at least in regions, in such a manner that said free end region of said capillary element directly adjoins said container outlet opening.

27. The device according to claim 25, wherein said at least one container outlet opening is closed by way of an openable cover.

28. The device according to claim 25, wherein said container is realized as a container which is open on one side, said covering wall of which is realized by a cap which realizes a separate component and constituent of said cover and closes said container, wherein said at least one container outlet opening is realized in said cap.

29. The device according to claim 1, wherein said container is produced from a plastics material and/or comprises an elongated shape and/or comprises a shape that is rectangular in cross section.

30. The device according to claim 1, wherein said capillary element is a wick.

31. The device according to claim 1, wherein said container comprises at least one fixing device, by means of which said capillary element is held in an interior of said container in an accurate position and condition.

32. The device according to claim 1, wherein said capillary element comprises an L-shaped form, with a first L leg, which extends in an interior of said container in a direction of a container vertical axis, and with a second L leg which projects therefrom at an angle and is assigned to a container outlet opening.

33. The device according to claim 32, wherein said fixing device is formed by at least one of said following measures:

said first L leg, when seen in a transverse direction of said container, is held by inside wall-side projections which are located on opposite sides of said first L leg, said first L leg and/or said second L leg, when seen at said bottom of said container, is or are held between a front wall and a rear wall of said container, said second L leg engages behind an inside wall-side projection or a projection which is formed by an inside part region of a support surface for said electrical heating element, said first L leg, when seen in said direction of said vertical axis, is supported on oppositely situated container walls.

34. The device according to claim 1, wherein said electrical connection element comprises a decorative element which is releasably or non-releasably connected to said same, said decorative element being a decorative cover and/or a decorative plate, which, when viewed from a visible side of the device, covers said container in said mounted state thereof at least in regions.

35. A container for receiving volatile substances, the container comprising:

at least one capillary element which is arranged in said container and is in contact with a substance to be dispensed from the container and conveying the substance by capillary action to at least one substance dispensing region;

at least one electrical heating element disposed to adjoins said at least one capillary element and being a constituent part of the container, and said electrical heating element being an electrical resistance element and having a resistance layer as heating layer which is assigned to a capillary element region to be heated and/or is film-like an electrical contact device configured to electrically and releasably connect said at least one electrical heating element to an electrical connection element for supplying power to said at least one electrical heating element, wherein said electrical connection element is releasably connectable to the container;

said resistance layer being arranged directly or indirectly with an interposition of at least one intermediate layer in a heat transfer region on an outside surface of a container wall, which is produced at least in said region from a heat conducting material, and in said heat transfer region, said capillary element region to be heated abuts against an inside surface of said container wall in a bearing connection, such that said electrical heating element transfers heat to said container wall by means of heat conduction and from there to said capillary element region to be heated;

a support, which is realized integrally and/or in a plate-shaped manner and/or with two sides from a heat-conducting material and having an inside part region, which is assigned to said capillary element region of said capillary element to be heated and consequently to an interior of said container and on which said capillary element region to be heated rests and/or is fastened in a capillary element support region, and said support having an outer part region, which is remote from an inside capillary element support region and is consequently assigned to said outside region of said container and on which said electrical heating element is arranged and/or fastened for heat-conducting thermal contact.

* * * * *